(12) United States Patent
Zappacosta et al.

(10) Patent No.: US 9,980,824 B2
(45) Date of Patent: May 29, 2018

(54) INTERVERTEBRAL IMPLANTS AND RELATED METHODS OF USE

(71) Applicant: Globus Medical Inc., Audubon, PA (US)

(72) Inventors: Jason Zappacosta, Philadelphia, PA (US); Mark Fromhold, Ardmore, PA (US); Jason Gray, East Greenville, PA (US); Michael Hunt, Philadelphia, PA (US); Chris Saville, Morgantown, PA (US); Robert Rhoads, North Wales, PA (US); Michael Evangelist, Pottstown, PA (US); John Perkins, Pottstown, PA (US); Nick Padovani, Arlington, VA (US)

(73) Assignee: Globus Medical, Inc., Audubon, PA (US)

( * ) Notice: Subject to any disclaimer, the term of this patent is extended or adjusted under 35 U.S.C. 154(b) by 255 days.

(21) Appl. No.: 14/476,439

(22) Filed: Sep. 3, 2014

(65) Prior Publication Data

US 2016/0058565 A1 Mar. 3, 2016

(51) Int. Cl.
*A61F 2/44* (2006.01)
*A61F 2/46* (2006.01)
*A61F 2/30* (2006.01)

(52) U.S. Cl.
CPC .......... *A61F 2/4455* (2013.01); *A61F 2/4465* (2013.01); *A61F 2/4611* (2013.01); *A61F 2002/305* (2013.01); *A61F 2002/3008* (2013.01); *A61F 2002/30179* (2013.01); *A61F 2002/30308* (2013.01); *A61F 2002/30433* (2013.01); *A61F 2002/30604* (2013.01); *A61F 2002/30677* (2013.01); *A61F 2002/30787* (2013.01); *A61F 2002/30797* (2013.01); *A61F 2002/30836* (2013.01); *A61F 2002/30841* (2013.01); *A61F 2002/30845* (2013.01); *A61F 2002/30884* (2013.01); *A61F 2002/4475* (2013.01); *A61F 2002/4627* (2013.01)

(58) Field of Classification Search
CPC .............................. A61B 17/84; A61B 17/846
USPC ...................... 606/246–249; 623/17.11–17.16
See application file for complete search history.

(56) References Cited

U.S. PATENT DOCUMENTS

| | | | | |
|---|---|---|---|---|
| 5,053,035 | A * | 10/1991 | McLaren | A61B 17/7208 606/62 |
| 7,731,753 | B2 * | 6/2010 | Reo | A61F 2/442 623/17.12 |
| 9,039,774 | B2 * | 5/2015 | Chataigner | A61F 2/442 606/86 A |

(Continued)

*Primary Examiner* — Ellen C Hammond
*Assistant Examiner* — Christina Negrellirodriguez

(57) ABSTRACT

A method of implanting an intervertebral spacer may include positioning the intervertebral spacer within an intervertebral space defined by adjacent vertebral bodies. The intervertebral spacer may include a plurality of bores, and each of the plurality of bores may be configured to receive either a linear fastening element or a curvilinear fastening element. The method also may include selecting a first fastening element from a group including linear fastening elements and curvilinear fastening elements, and inserting the first fastening element into a first bore of the plurality of bores such that the first fastening element is inserted into one of the adjacent vertebral bodies to secure the intervertebral spacer within the intervertebral space.

18 Claims, 17 Drawing Sheets

(56) References Cited

U.S. PATENT DOCUMENTS

| | | | | |
|---|---|---|---|---|
| 2004/0068258 | A1* | 4/2004 | Schlapfer | A61B 17/70 606/261 |
| 2006/0136063 | A1* | 6/2006 | Zeegers | A61B 17/0642 623/17.14 |
| 2009/0105832 | A1* | 4/2009 | Allain | A61B 17/0642 623/17.16 |
| 2010/0185289 | A1* | 7/2010 | Kirwan | A61F 2/4455 623/17.11 |
| 2011/0230971 | A1* | 9/2011 | Donner | A61B 17/70 623/17.16 |
| 2012/0116465 | A1* | 5/2012 | Elahinia | A61B 17/8625 606/310 |
| 2012/0265259 | A1* | 10/2012 | LaPosta | A61B 17/8894 606/86 A |
| 2013/0150968 | A1* | 6/2013 | Dinville | A61F 2/447 623/17.16 |
| 2014/0088711 | A1* | 3/2014 | Chin | A61F 2/30749 623/17.16 |
| 2015/0057754 | A1* | 2/2015 | Reed | A61F 2/4611 623/17.16 |
| 2015/0209089 | A1* | 7/2015 | Chataigner | A61B 17/7064 623/17.16 |
| 2015/0320466 | A1* | 11/2015 | Kennedy | A61B 17/8605 606/308 |

* cited by examiner

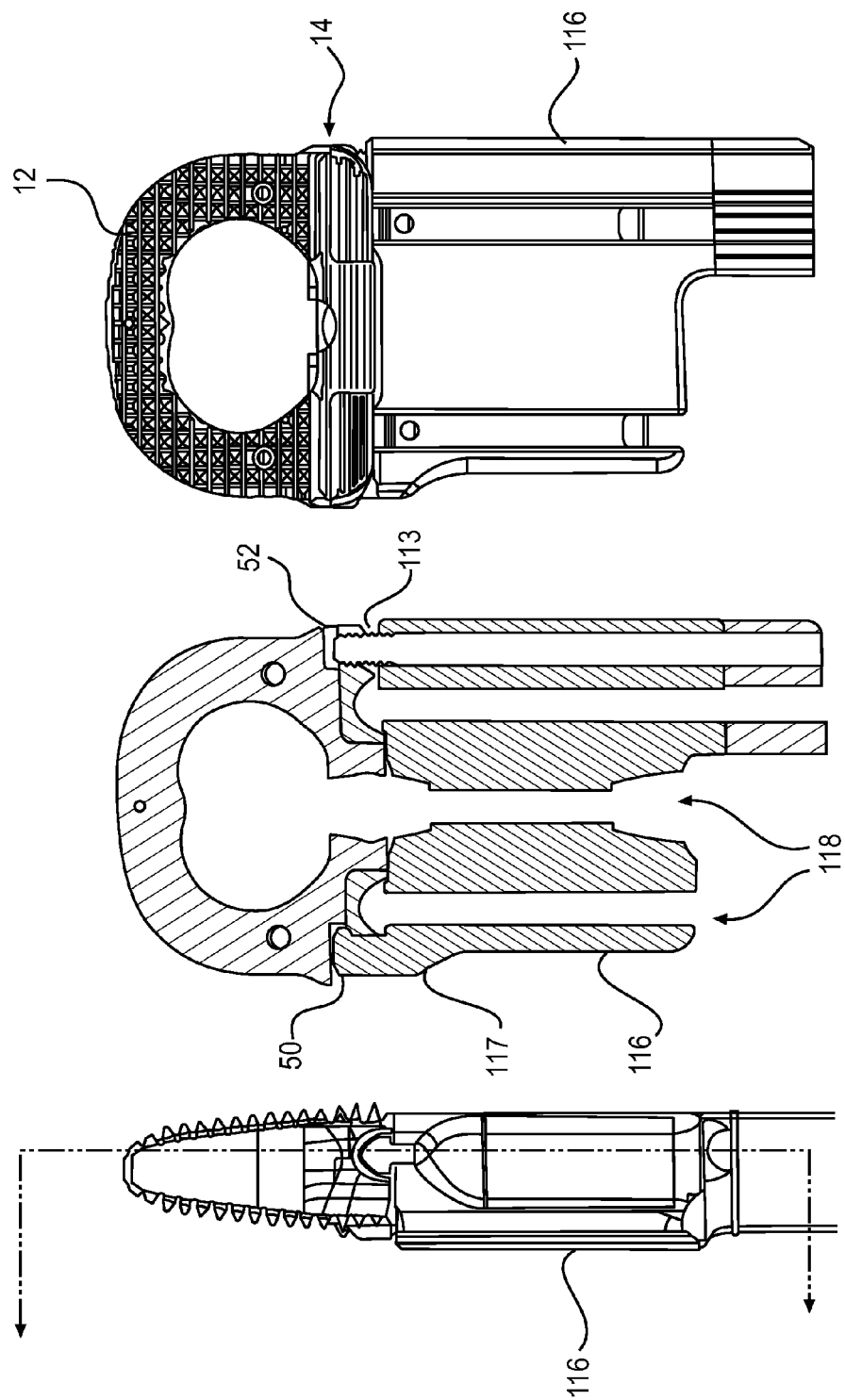

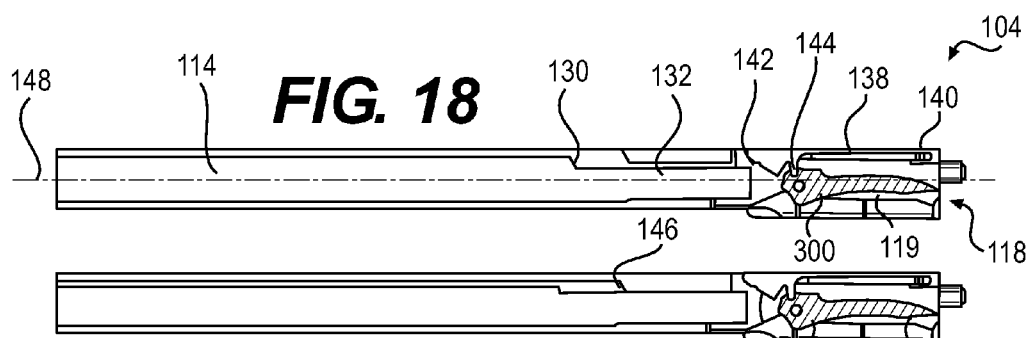
FIG. 18
FIG. 19
FIG. 20
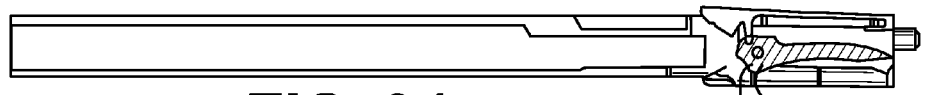
FIG. 21
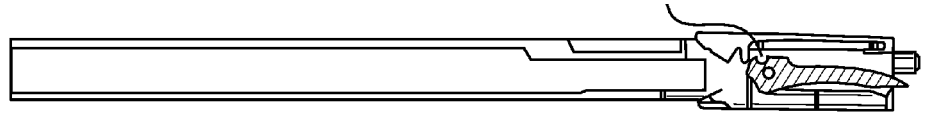
FIG. 22
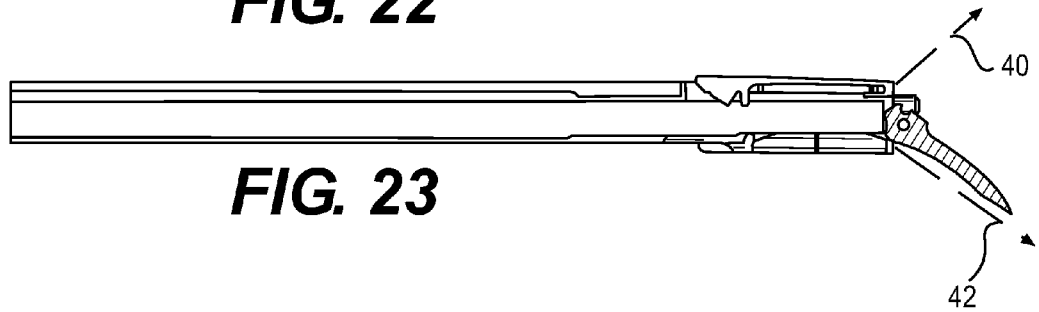
FIG. 23

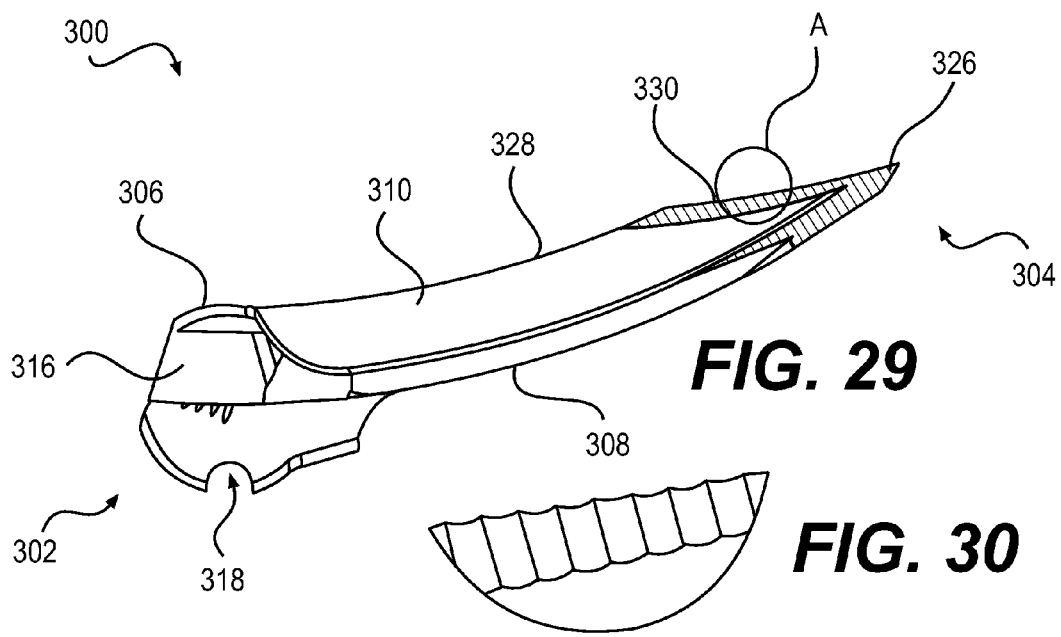
FIG. 29
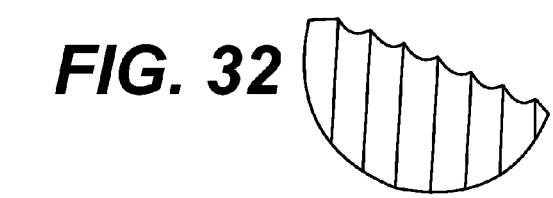
FIG. 30
FIG. 32
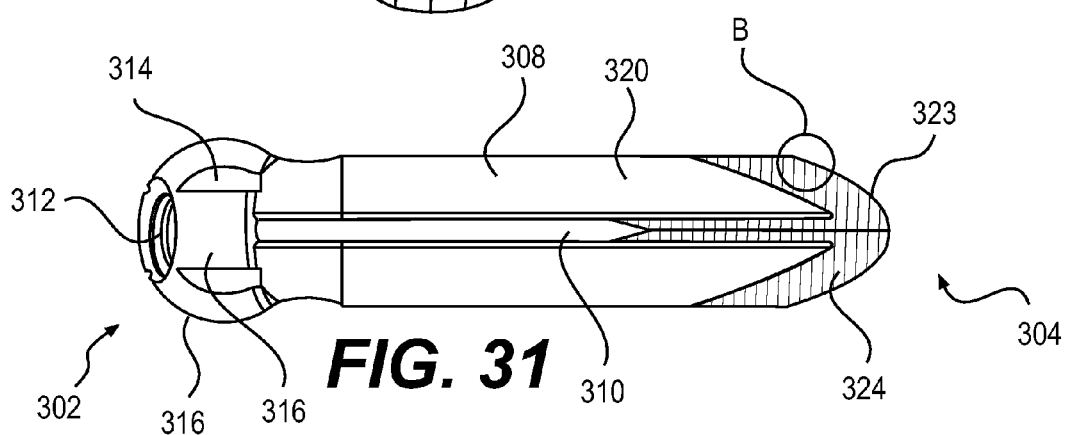
FIG. 31

INTERVERTEBRAL IMPLANTS AND RELATED METHODS OF USE

FIELD OF THE INVENTION

Various examples of the present disclosure relate generally to vertebral implants and related systems and methods. More specifically, the present disclosure relates to vertebral anchors, spacers, devices, systems, and methods for repairing and/or replacing intervertebral discs of a patient.

BACKGROUND

A common procedure for handling pain associated with intervertebral discs that have become degenerated due to various factors such as trauma or aging is the use of intervertebral spacers to, e.g., fuse one or more adjacent vertebral bodies. Generally, to fuse adjacent vertebral bodies, the native intervertebral disc is first partially or fully removed. An intervertebral spacer is then typically inserted between neighboring vertebral bodies to maintain normal disc spacing and restore spinal stability, thereby facilitating an intervertebral fusion.

There are a number of known conventional intervertebral spacers and methodologies in the art for accomplishing the vertebral fusion. These include screw and rod arrangements, solid bone implants, and intervertebral spacers which include a cage or other implant mechanism that may be packed with bone and/or bone growth inducing substances. These devices may be implanted between adjacent vertebral bodies in order to fuse the vertebral bodies together, potentially alleviating any associated pain.

However, there are drawbacks associated with the known conventional vertebral spacers and methodologies. Some conventional vertebral spacers may not be optimally configured for insertion into irregular or curved portions of the spine. For example, at the most caudal or most cephalad cervical disc spaces or caudal lumbar levels, conventional, angled instruments used to install conventional fasteners may interfere with the chin, chest, or other portion of a patient's anatomy, making insertion of conventional fastening members difficult.

SUMMARY OF THE DISCLOSURE

The present disclosure relates to examples of intervertebral spacers and related methods of use. A method of implanting an intervertebral spacer may include positioning the intervertebral spacer within an intervertebral space defined by adjacent vertebral bodies. The intervertebral spacer may include a plurality of bores, and each of the plurality of bores may be configured to receive either a linear fastening element or a curvilinear fastening element.

BRIEF DESCRIPTION OF THE FIGURES

The accompanying drawings, which are incorporated in and constitute a part of this specification, illustrate various exemplary embodiments and together with the description, serve to explain the principles of the disclosed examples.

FIGS. 15-17 depict the insertion device of FIG. 10 coupled with an intervertebral anchor in accordance with an example of the present disclosure.

FIGS. 18-23 depict an exemplary tool and method of installing a vertebral anchor in accordance with an example of the present disclosure.

FIG. 29 is a side view of a vertebral anchor in accordance with an example of the present disclosure.

FIG. 30 is an enlarged view of detail A in FIG. 29, illustrating a distal portion of the vertebral anchor of FIG. 29.

FIG. 31 is a top view of the vertebral anchor of FIG. 29.

FIG. 32 is an enlarged view of detail B in FIG. 31, illustrating a distal portion of the vertebral anchor of FIG. 31.

DETAILED DESCRIPTION

Figure 1:
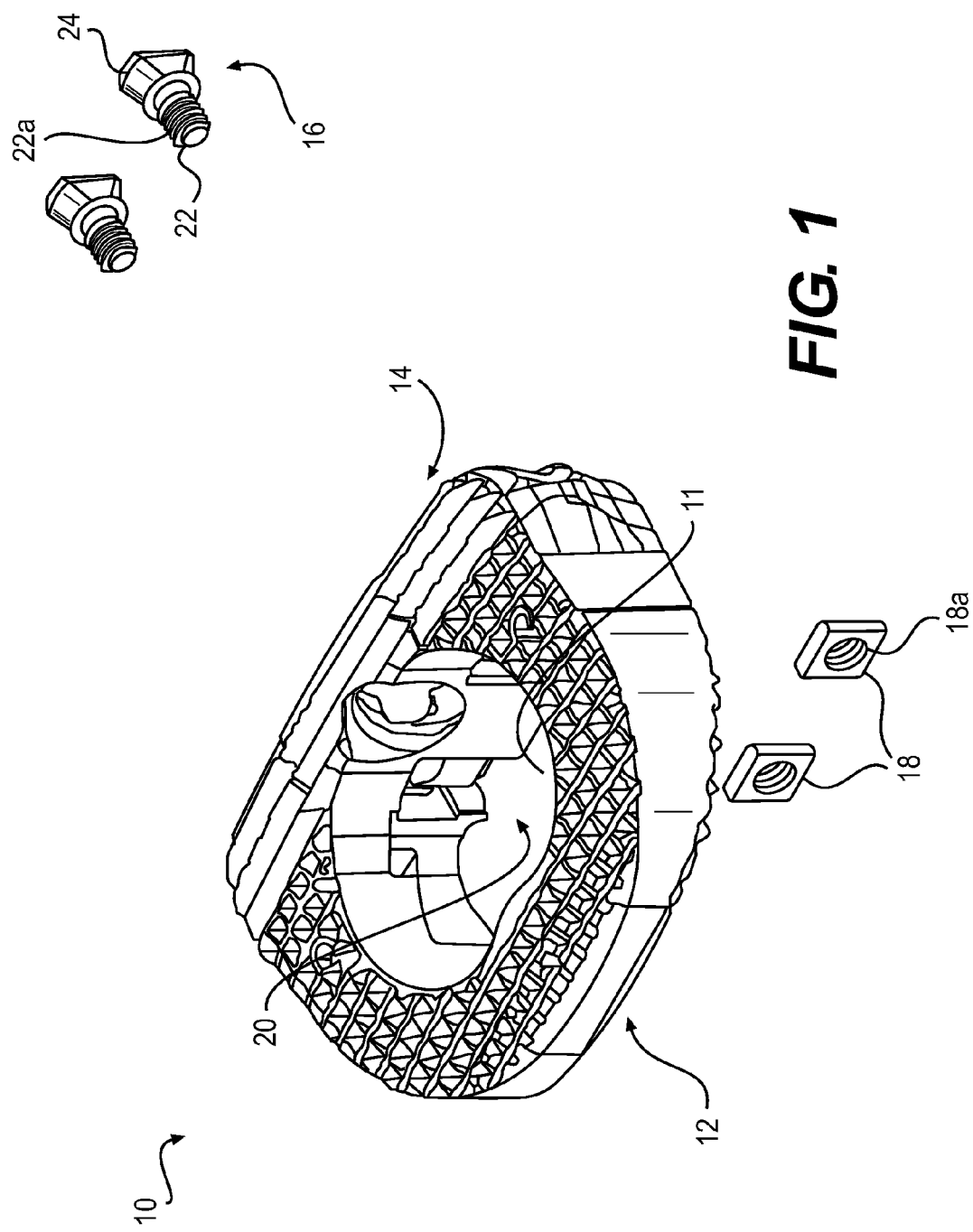
FIGS. 1-8 illustrate various views of a vertebral spacer in accordance with a first exemplary embodiment of the present disclosure.

Reference will now be made in detail to embodiments of the present disclosure, examples of which are illustrated in the accompanying drawings. Wherever possible, the same reference numbers will be used throughout the drawings to refer to the same or like parts.

FIGS. 1-8 illustrate the different views of an intervertebral spacer 10 according to the present disclosure. The intervertebral spacer 10 as shown in FIGS. 1-8 may be, e.g., a stand-alone anterior lumbar interbody spacer used to provide structural stability in skeletally mature individuals following discectomies. These intervertebral spacers may be available in various heights and geometric configurations to fit the anatomically needs of a wide variety of patients. Specifically, FIGS. 1-8 illustrate one embodiment of an intervertebral spacer 10. Intervertebral spacer 10 may be generally positioned in the intervertebral space between two adjacent vertebral bodies. As shown in the figures, intervertebral spacer 10 may include a spacer portion 12 and a plate portion 14. In one example, the spacer portion 12 may include a graft window 11 for the placement of, e.g., bone graft or bone-growth inducing material, to enhance fusion between two adjacent vertebral bodies.

The spacer portion 12 can be comprised of any material that is conducive to the enhancement of fusion between the two adjacent vertebral bodies. In one particular embodiment, the spacer portion 12 is made of PEEK material, which may be physiologically compatible. It should be noted that any other materials that are physiologically compatible also may be used. The spacer portion 12 may include tantalum pins that enable radiographic visualization, or other suitable radiographic markers. The spacer portion 12 further may include superior and inferior surfaces that are provided with a plurality of geometric configurations, such as, e.g., protrusions 13 (e.g., ribs, bumps, other textures, or the like). The superior and inferior surfaces of the spacer portion 12 may be bi-convex for greater contact with the vertebral endplates of the adjacent vertebral bodies. The protrusions 13 can be configured to be any size or shape for further anchoring the spacer portion 12 to each of the adjacent vertebral bodies. Protrusions 13 on the superior and inferior surfaces of each implant may grip the endplates of the adjacent vertebral bodies to aid in expulsion resistance.

Figure 14:
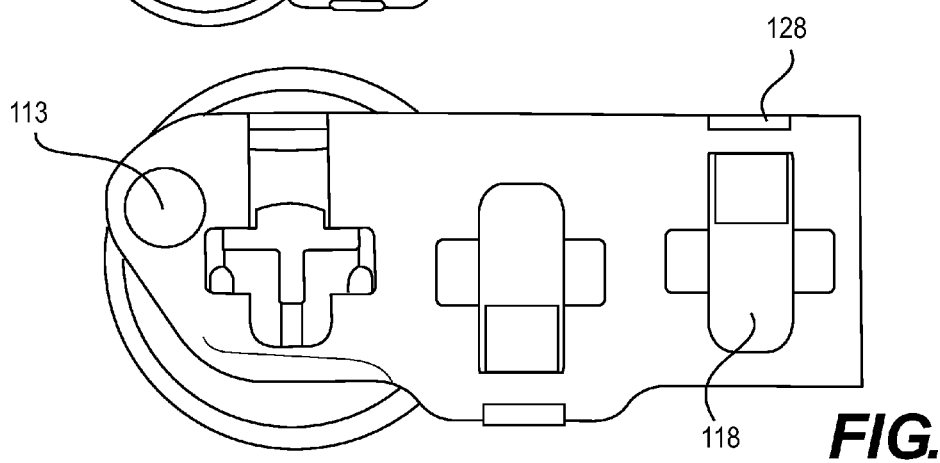
Figure 24:
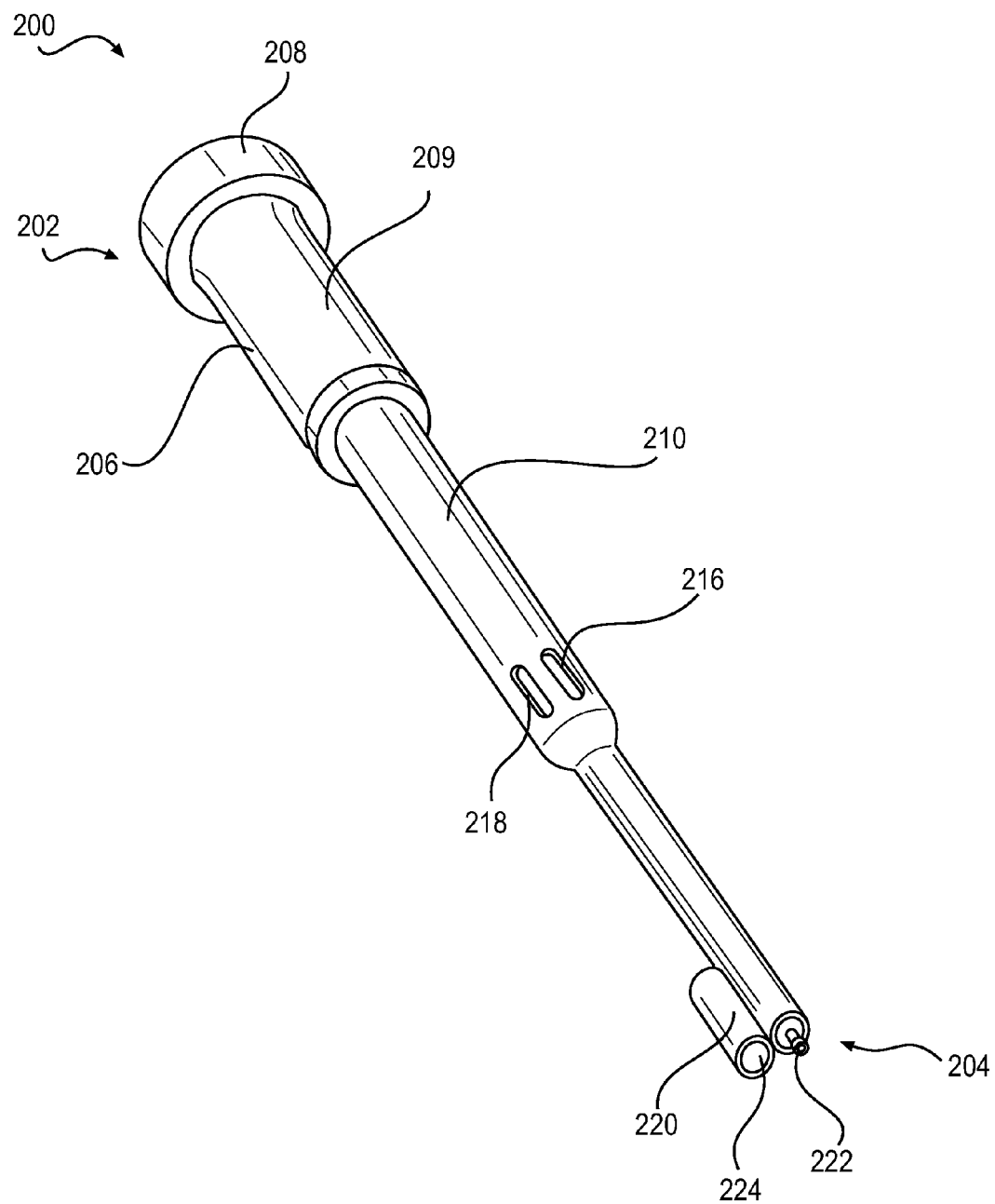
FIG. 24 is a perspective view of another exemplary insertion device in accordance with an example of the present disclosure.

The plate portion 14 can also be comprised of any physiologically compatible material. In one example, the plate portion 14 of the intervertebral spacer 10 may be formed from titanium. The plate portion 14 may include at least one bore 26. In some embodiments, plate portion 14 may include a plurality of bores 26, in such embodiments, one or more bores 26 may or may not include threads for receiving corresponding threads on a fastener. That is to say, in some examples, one or more of bores 26 may interact with features (e.g., threads) configured to receive features (e.g., corresponding threads) of a fastening member (e.g., a linear bone screw) to be disposed therethrough. Bores 26 may be substantially linear. Such a configuration allows bores 26 to receive both linear fastening members and curvilinear fastening members. That is, a given bore 26 may be configured to receive either a linear fastening member (e.g., a screw) or a curvilinear fastening member (as discussed below in greater detail) at the discretion of an operator, surgeon, physician, or the like. In one embodiment, e.g., bores 26 may include one or more features, e.g., threads, that are configured to engage with threads of a fastening member (e.g., a linear fastening member or bone screw). Further, in some examples, a curvilinear fastening member disposed through a given bore 26 may be configured so as not to engage the threads of the given bore 26. Still further, each bore 26 may include locking features configured to engage with complimentary features on a curvilinear fastening member to prevent the curvilinear fastening member from rotating when disposed through the bore 26. In one example, each bore 26 may be defined by a circumferential wall having a recess (not shown) disposed therein. The recess may be configured to receive a protrusion extending from the curvilinear fastening member to prevent the curvilinear fastening member from rotating. In one example, three bores 26 may be provided. In yet another example, two outer bores 26 may surround a central bore 26. The two outer bores 26 may be angled to guide a fastening member (e.g., a vertebral anchor 300 described with reference to FIGS. 29-36, or a bone screw) along a first trajectory 40 shown in FIG. 14 (e.g., toward one of a superior or inferior surface of intervertebral spacer 10), while the central bore 26 may be angled to guide a fastening member along a second trajectory 42 (e.g., toward the other of the superior and inferior surface of intervertebral spacer 10), and vice versa. In some examples, all bores 26 may guide respective fasteners along the same trajectory. The bores 26 can accommodate a straight longitudinal fastening member (e.g., a screw, pin, or the like) and/or a fastening member exhibiting a curvature (e.g., vertebral anchor 300 shown in FIGS. 1-8). In some examples, a combination of vertebral anchors 300 and conventional screws may be used to install the same intervertebral spacer 10.

Figure 8:
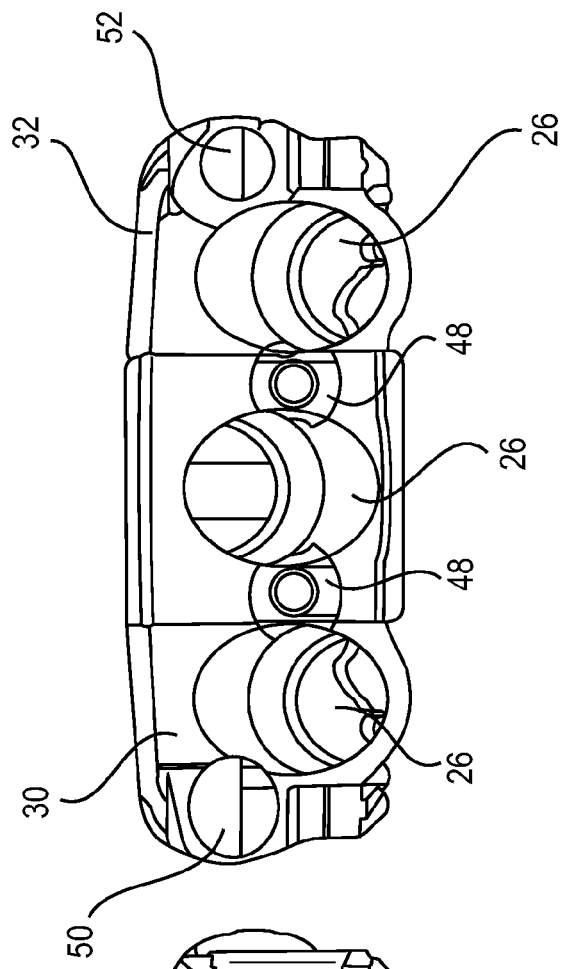
Figure 7:
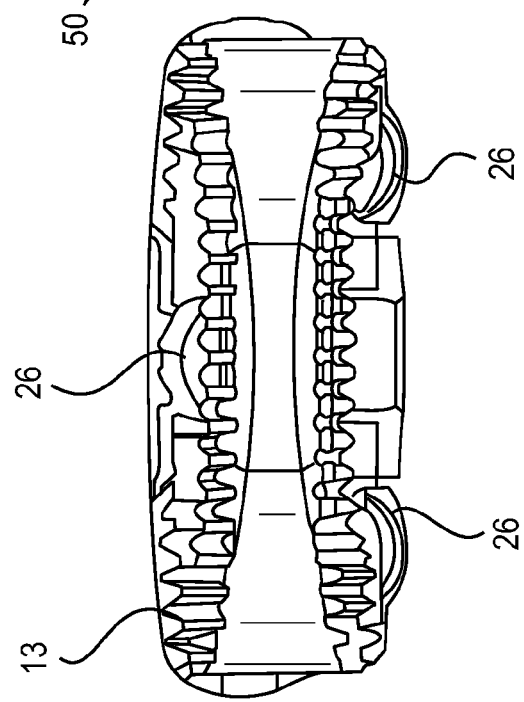

Also, in the plate portion 14 of the intervertebral spacer 10, a fastener back out prevention mechanism may be provided. The fastener back out prevention mechanism may include one or more screws 16, each having a head portion 24 and a shank 22 having threads 22a. Shank 22 may be received by a bore 48 (shown in FIG. 8) that extends from a first side 44 of plate portion 14 toward a second side 46 of plate portion 14. Shank 22 also may be received by a nut 18 having a threaded bore 18a (shown in FIG. 1). Nut 18 may have a substantially rectangular cross-section, or may have another suitable shape. Nut 18 may be secured within a recess 20 on second side 46 of plate portion 14. However, it is contemplated that screws 16 may be secured to plate portion 14 by any other suitable mechanism. Head portion 24 may have a generally rectangular cross-section such that it may prevent a fastening member from backing out of bores 26 when disposed in certain configurations (e.g., a blocking configuration). For example, referring to FIG. 8, the head portion 24 of screw 16 may extend over, cover, and/or block at least a portion of the opening of one more of bores 26, preventing a fastening member (e.g., a vertebral anchor 300 or a bone screw) extended through a bore 26 from backing out of plate portion 14 and a vertebral body. It is also contemplated that in some examples, a single head portion 24 may extend at least partially over two adjacent bores 26 (e.g., both an outer bore 26 and a central bore 26), thereby blocking the openings of more than one bore 26 at the same time while disposed in a blocking configuration. Head portion 24 can be moved from the blocking configuration to a non-blocking configuration by rotating head portion by, e.g., 90 degrees or another suitable measure. While depicted as rectangular, it is contemplated that head portion 24 may be formed in other suitable elongate shapes, such as, e.g., cylindrical or the like. In the example of FIG. 8, plate portion 14 may be configured to receive two screws 16 in bores 48 (shown in FIG. 8). Each of the screws 16 may be configured to block fastening members disposed in an outer bore 26 and a central bore 26, such that each outer bore 26 is blocked by a single screw 16, and the central bore 26 is blocked by both screws 16.

Figure 2:
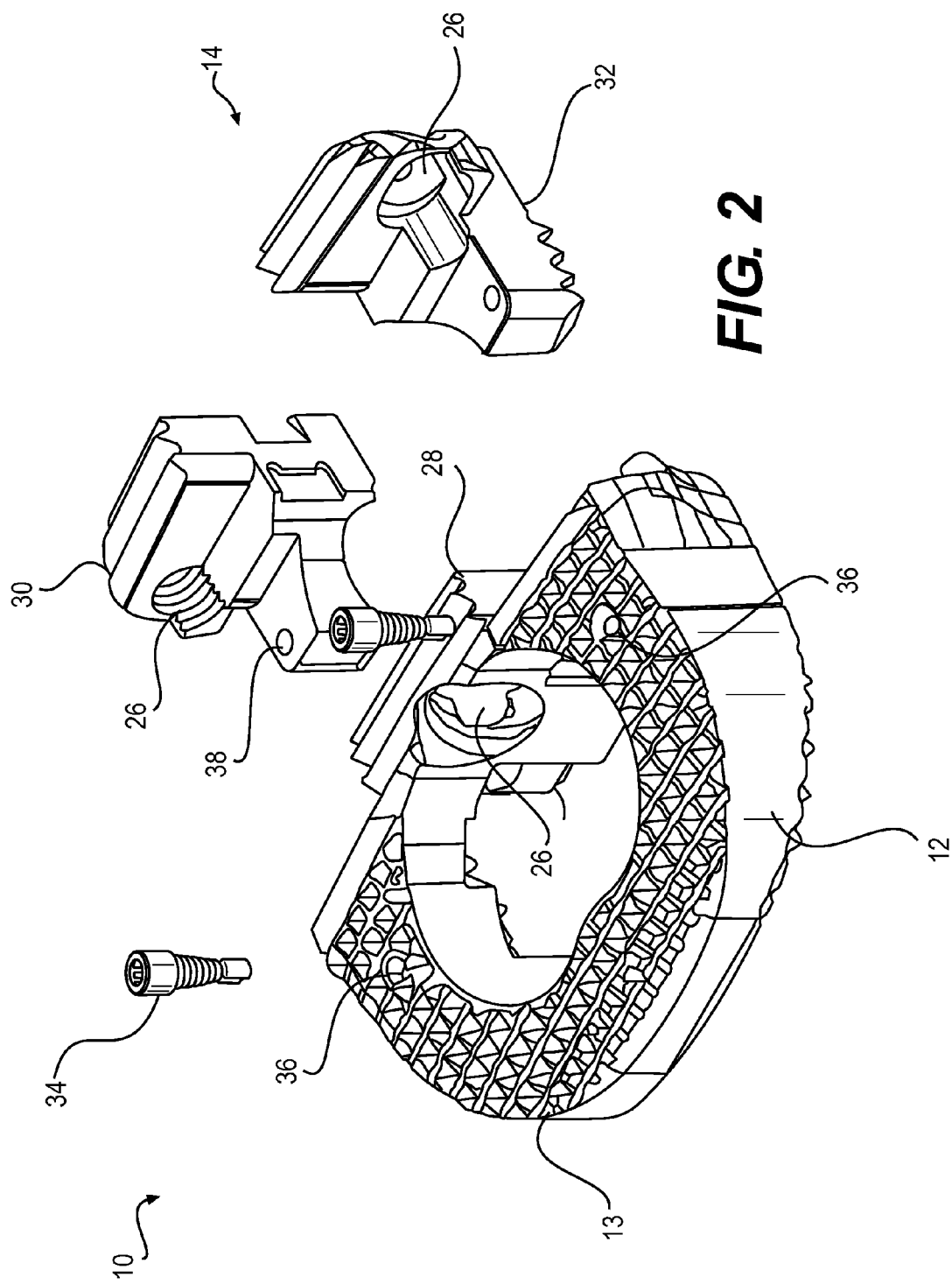
Figure 4:
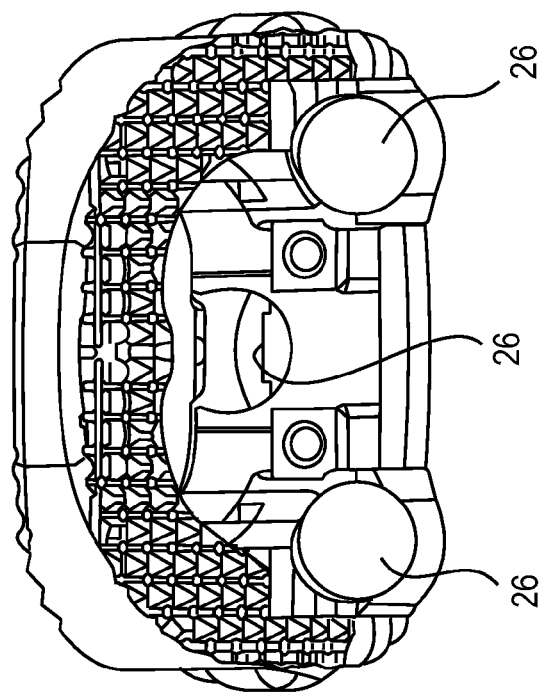
Figure 3:
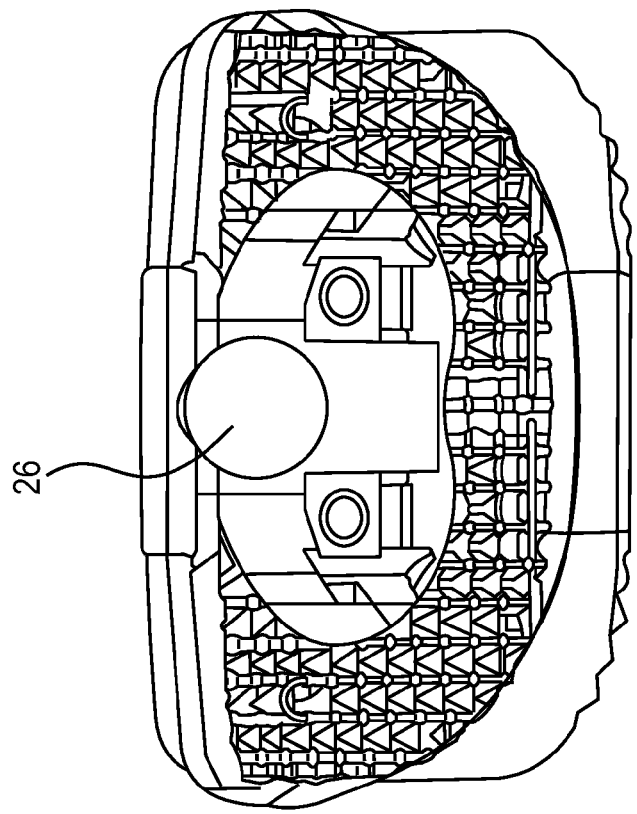
Figure 6:
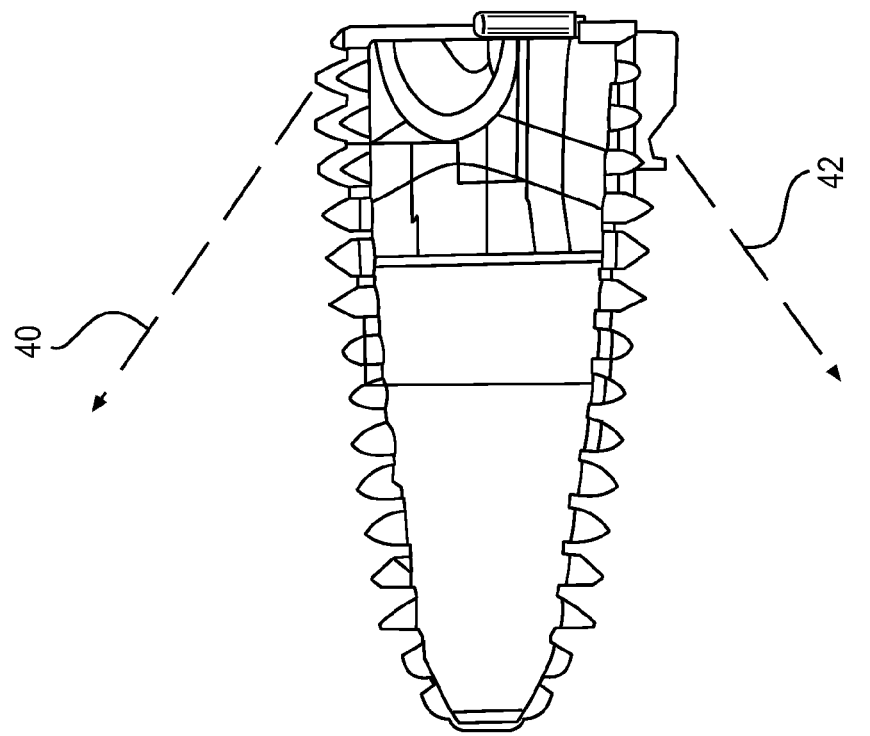
Figure 5:
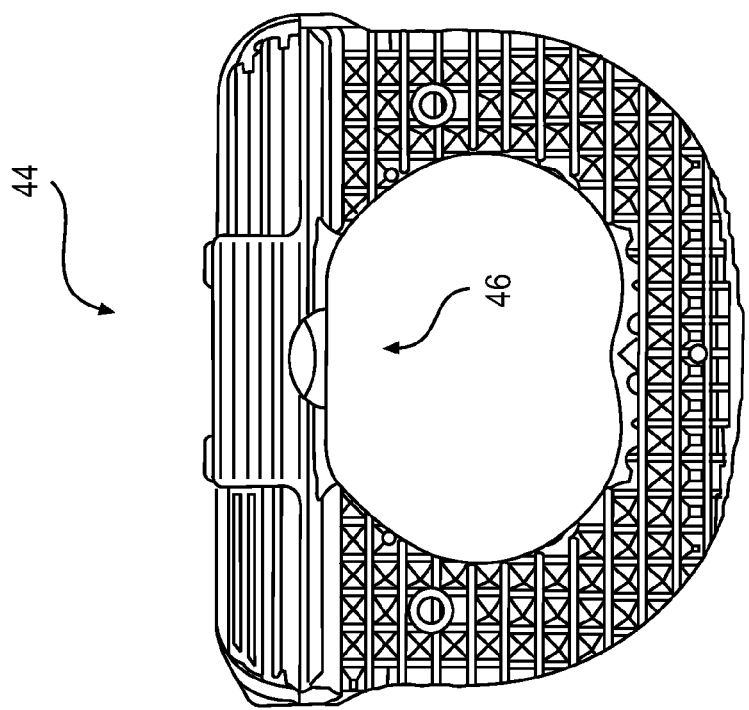

A coupling mechanism may connect the spacer portion 12 and the plate portion 14 rigidly to each other, if desired. With reference to FIG. 2, the coupling mechanism may include one or more fastening members 34 that extend through corresponding recesses 36 disposed through spacer portion 12 and recesses 38 disposed through at least a portion of plate portion 14. In one example, a fastening member 26 may extend through the superior and inferior surfaces of spacer portion 12 (via a recess 36) and may be received by recess 38 of plate portion 14, thereby coupling spacer portion 12 and plate portion 14. It is contemplated that recess 38 and fastening member 26 may include complimentary mating features (e.g., threads) to facilitate coupling of plate portion 14 to spacer portion 12. In the example shown in FIG. 2, plate portion 14 may be formed by three bore sections 28, 30, and 32. Bore sections 28, 30, and 32 may either be integrally formed or detachable with spacer portion 12. In one example, bore section 28 may be integral with spacer portion 12 while bore sections 30 and 32 may be detachable with spacer portion 12 via fastening members 34 and recesses 36 and 38. In one example, the detachable bore sections 30 and 32 may include the outer bores 26 that are configured to direct a vertebral anchor 300 or bone screw along the first exit trajectory 40, and the bore section 28 may include the central bore 26 configured to direct a vertebral anchor 300 or bone screw along the second exit trajectory 42. Further, one or more of the bore sections 28, 30, and 32 may include a portion configured to extend through a slot of or other opening in spacer portion 12. In such examples, the recesses 36, 38, or the like associated with the bore sections may align with recesses formed through spacer portion 12 to receive fastening members 34.

Plate portion 14 also may include coupling features for coupling plate portion 14 to an anchor insertion device 100 which will be described further with reference to FIGS. 10-23. As shown in FIG. 8, plate portion 14 may include a channel (e.g., a snap-fit channel) 50 having an opening disposed in an outer surface of plate portion 14. The channel 50 may be configured to receive an extension (e.g., a cantilever and/or snap-fitting extension) of anchor insertion device 100 to couple plate portion 14 to the insertion device 100. In some examples, channel 50 may be disposed in bore section 30 of plate portion 14. With continuing reference to FIG. 8, channel 50 may have a generally ovular opening, although other suitable opening configurations such as, e.g., circular, square, rectangular, star-shaped, or the like are also contemplated. Plate portion 14 also may include a bore 52 (e.g., a threaded bore) having an opening that is also disposed through an outer surface of plate portion 14. In one example, bore 52 may be disposed through bore section 32 of plate portion 14.

In an exemplary method, a physician, surgeon, or other suitable operator may remove, among other things, the native intervertebral disc between two vertebral bodies. The operator then may select a given intervertebral spacer, e.g., intervertebral spacer 10, to replace the removed native intervertebral disc. Based on the geometry of the surrounding vertebral bodies and/or anatomy, the operator may determine that linear fastening members (e.g., linear bone screws), curvilinear fastening members (e.g., vertebral anchors 300 or 400), or a combination of linear fastening members and curvilinear fastening members, will provide optimal fit and securement of intervertebral spacer 10 between the vertebral bodies. For example, the curvature of the spine at one or more of the vertebral bodies may substantially inhibit the use of the tools and driving members used to install linear fastening members. In such examples, curvilinear fastening members may be selected to secure intervertebral spacer 10. The curvilinear fastening members may be installed through the same linear bore 26 that may be configured to receive linear fastening members. Further, the curvilinear fastening members may be installed through the linear bore with a positioning member (described with reference to FIG. 10) utilizing a guide member that can be extended only along a linear track.

In one example, one or more curvilinear fasteners may be used to secure intervertebral spacer 10 to one vertebral body defining an intervertebral space, while one or more linear fasteners may be used to secure intervertebral spacer 10 to the other vertebral body defining the intervertebral space. For example, curvilinear fasteners may be extended through outer bores 26 while a linear fastener is extended through central bore 26. Alternatively, linear fastening members may be extended through outer bores 26 while a curvilinear fastening member is extended through central bore 26. In yet another example, both linear and curvilinear fastening members may be used to secure the same intervertebral spacer into a given vertebral body. That is, a curvilinear fastening member may be extended through one outer bore 26, while a linear fastening member is extended through the other outer bore 26.

Figure 9:
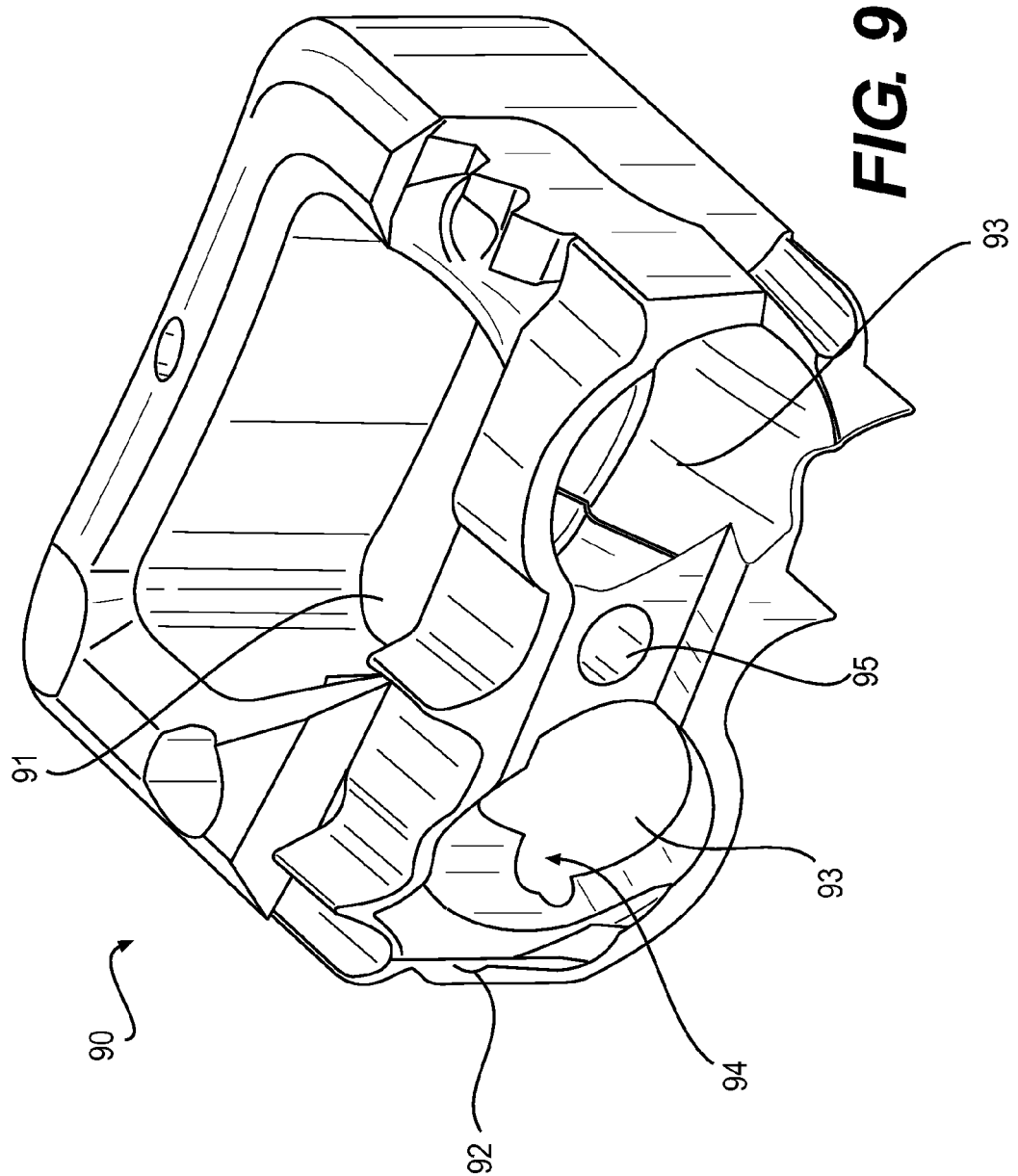
FIG. 9 is a perspective view of another exemplary intervertebral spacer in accordance with an example of the present disclosure.

FIG. 9 depicts an intervertebral spacer 90 in accordance with an example of the present disclosure. In some examples, intervertebral spacer 90 may be substantially similar to intervertebral spacer 10, or may be another suitable intervertebral spacer. In the example shown in FIG. 9, spacer 90 may be a generally rectangular spacer defining a cavity 91. Cavity 91 may be packed with bone graft or bone-growth inducing materials. Spacer 90 may include one or more of inferior surfaces, superior surfaces, biconvex surfaces, among others. In some examples, the surfaces of spacer 90 or any other bone contacting surface described in the present disclosure may include one or more of teeth, ridges, friction increasing elements, keels, or gripping or purchasing projections.

Figure 25:
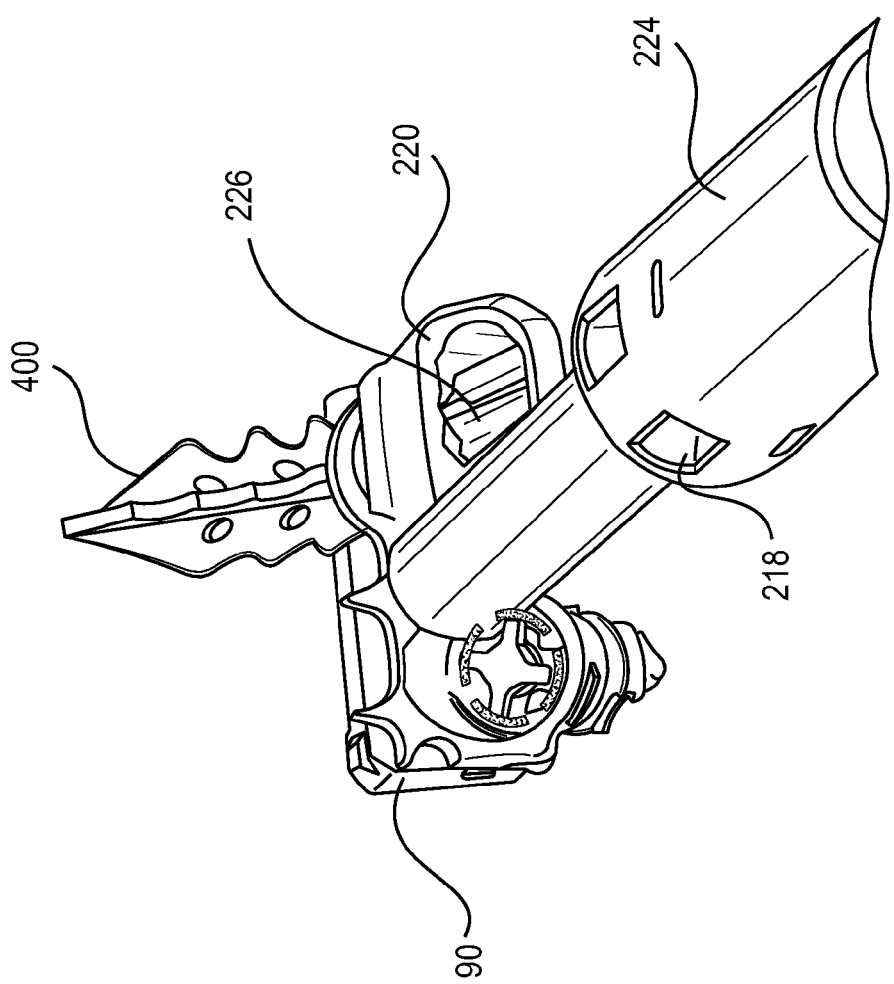
FIG. 25 is a perspective view of an insertion device and an intervertebral spacer having a plurality of fasteners in accordance with an example of the present disclosure.

Spacer 90 may include a plate portion 92 that may include one or more features described with reference to plate portion 14 of intervertebral spacer 10. In one example, one or more bores 93 may disposed through plate portion 92. Though FIG. 9 depicts two bores 93, those of ordinary skill in the art will recognize that any suitable number of bores may be provided. Bores 93 may include one or more features described with reference to bores 26 of intervertebral spacer 10. The two bores 93 may be angled to guide a fastening member (e.g., a vertebral anchor 300 or a bone screw) along differing trajectories. For example, one bore 93 may be angled to urge a fastening member along a first trajectory (e.g., toward one of a superior or inferior surface of intervertebral spacer 90), while the other bore 93 may be angled to urge a fastening member along a second trajectory (e.g., toward the other of the superior and inferior surface of intervertebral spacer 90). The bores 93 can accommodate a straight longitudinal fastening member (e.g., a screw, pin, or the like) and/or a fastening member exhibiting a curvature (e.g., vertebral anchor 300 or 400). In some examples, a combination of vertebral anchors 300 or 400 and conventional screws may be used to install the same intervertebral spacer 90 as shown in FIG. 25. A circumferential wall defining bores 93 may further include one or more recesses 94 disposed therein. The one or more recesses 94 may be configured to receive one or more protrusions 460 disposed on a head portion 406 of a vertebral anchor 400 (described with reference to FIGS. 37-40). Thus, in some examples, recesses 94 may be partially-spherical to receive protrusions 460. However, it is contemplated that recesses 94 may be formed in any suitable shape configured to receive protrusions 460. Plate portion 92 also may include a bore 95 having an opening that is disposed through an outer surface of plate portion 92. The bore 95 may include one or more features, e.g., threads or other features to engage with an insertion device 200 described with further detail below. Intervertebral spacer 90 also may include one or more features configured to prevent fastening members from backing out of bores 93, such as, e.g., screws 16 described with reference to FIGS. 1-8.

Intervertebral spacer 90 may be inserted into an intervertebral space between two vertebral bodies in a substantially similar manner as intervertebral spacers 10. In one example, one or more curvilinear fasteners may be used to secure intervertebral spacer 90 to one vertebral body defining an intervertebral space, while one or more linear fasteners may be used to secure intervertebral spacer 90 to the other vertebral body defining the intervertebral space. For example, a curvilinear fastener may be extended through one bore 93 while a linear fastener is extended through the other bore 93.

Figure 10:
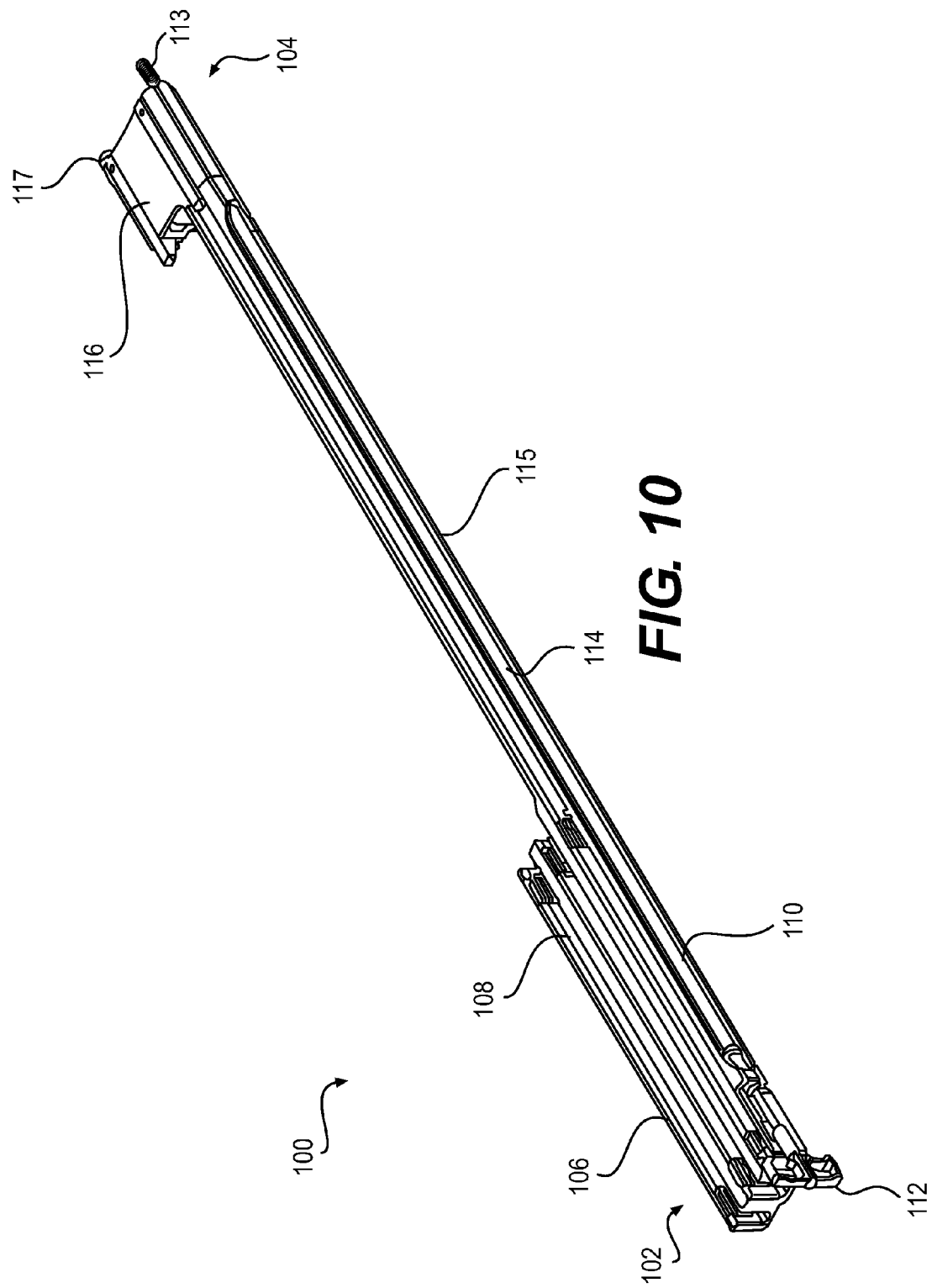
FIG. 10 is an insertion device in accordance with an example of the present disclosure.

An insertion device 100 is shown in FIG. 10, which may be used to position vertebral anchors 300 through a plate portion of an intervertebral spacer (e.g., plate portion 14 of intervertebral spacer 10) and through a vertebral body. Insertion device 100 may extend from a trailing end 102 toward a leading end 104. A trailing housing 106 may be disposed at trailing end 102 and may define one or more elongate channels 108. In the embodiment shown, three elongate channels 108 are shown, although any other suitable number of elongate channels 108 may be disposed through trailing housing 106. Each of elongate channels 108 may receive a guide member 110 therethrough. Guide member 110 may include a head portion 112 and an elongate portion 114 that extends away from the head portion 112. In some examples, head portion 112 may include one or more flattened and reinforced surfaces configured to receive the force of a striking member (e.g., a hammer or the like). Elongate portion 114 may be extended through one or more elongate channels 108 toward leading end 104. The distal or leading end of elongate portion 114 may include a stepped portion 132 (shown in FIG. 18). Stepped portion 132 may be separated from the remainder of elongate portion 114 by a vertical wall 130. In some examples, stepped portion 132 may include a smaller cross-sectional dimension (e.g., thickness or width) as compared to a remainder of elongate portion 114.

A connecting housing 115 may extend from trailing housing 106 toward an anchor housing 116 disposed at leading end 104. In some examples, connecting housing 115 may be an alignment shaft configured to align elongate channels 108 with a corresponding number of anchor channels 118 (see FIG. 11) disposed in anchor housing 116. In the embodiment shown in FIG. 10, connecting housing 115 may extend from only one of elongate channels 108 to couple trailing housing 106 to anchor housing 116. However, those of ordinary skill in the art will appreciate that a shaft 116 may extend from more than one elongate channel 108 toward anchor housing 116. Guide member 110 may extend through an elongate channel 108, through connecting housing 115, and into an anchor channel 118, where it may come into contact with a vertebral anchor 300 just before inserting the vertebral anchor 300 through a vertebral body, as described further with reference to FIGS. 18-23. In some examples, connecting housing 115 may merely align certain elongate channels 108 in trailing housing 106 with anchor channels 118 disposed in anchor housing 116. In such examples, elongate portion 114 of guide member 110 may exit a leading end of elongate channel 108 and extend through an open and unconfined space before entering a trailing end of an anchor channel 118.

Figure 11:
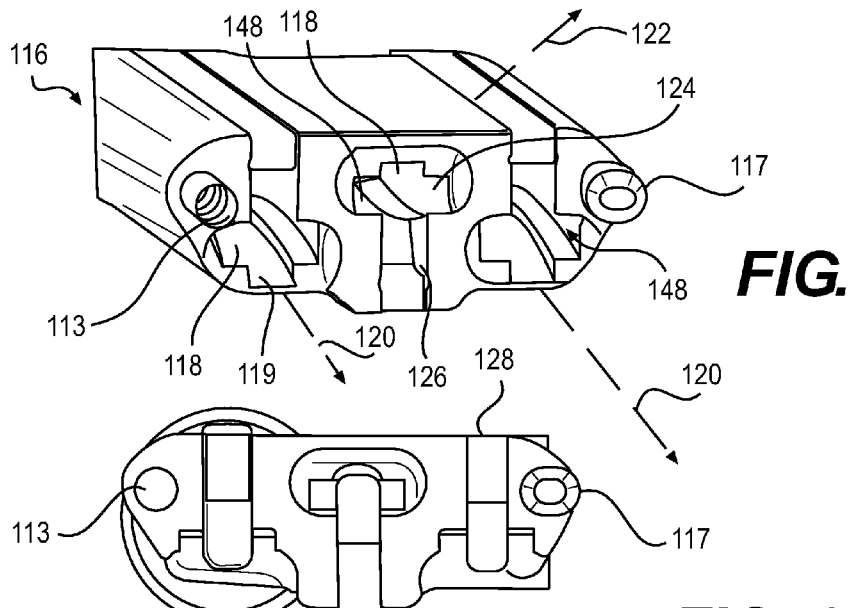
FIGS. 11-14 depict various end or cross-sectional views of the insertion device of FIG. 10.
Figure 12:
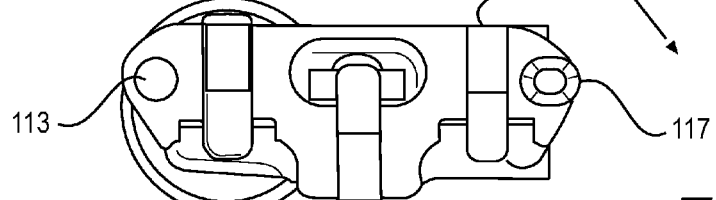
Figure 13:
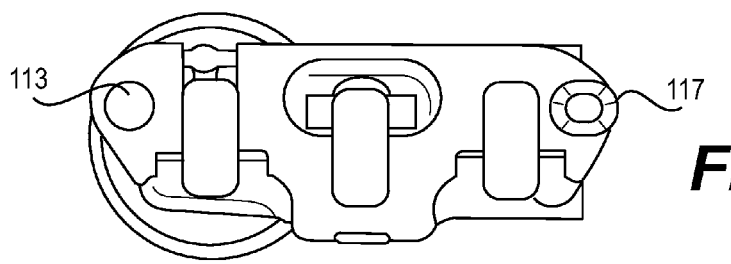

As best seen in FIG. 11, anchor housing 116 may include one or more anchor channels 118. Each anchor channel 118 may have a variable cross-section along the length of anchor housing 116. In some examples, a given cross-section of anchor channel 118 may be t-shaped or any another suitable cross-section. A curvature at the leading end of anchor channel 118 may be complimentary to certain portions of a curvilinear anchor (e.g., anchor 300 shown in FIG. 29). Those portions may include an elongate shank 308 and elongate fin 310, shown in FIGS. 29 and 31. That is, anchor channel 118 may be defined by a concave surface 119 that is complimentary to elongate shank 308 of vertebral anchor 300. For example, a laterally extending portion 148 of each channel 118 may be configured to complement and receive a curved elongate shank 308, and a vertically extending portion 126 of each channel 118 may receive a curved elongate fin 310. Thus, a vertebral anchor 300 may be disposed within each anchor channel 118 and may exit anchor channel 118 along a given exit trajectory. Some anchor channels 118 may urge a vertebral anchor 300 along a first exit trajectory 120 while other exit channels 118 may urge a vertebral anchor 300 along a second exit trajectory 122. First exit trajectory 120 may extend in a first vertical direction out of the leading end of anchor housing 116 while the second, different exit trajectory 122 may extend in a second vertical direction out of the trailing end of anchor housing 116. A given anchor housing 116 may include a plurality of anchor channels 118 that may direct all vertebral anchors 300 along the first exit trajectory 120, all vertebral anchors 300 along the second exit trajectory 122, or some vertebral anchors 300 along the first exit trajectory 120 and some vertebral anchors 300 along the second exit trajectory 122. Each of first and second trajectories 120 and 122 may intersect a longitudinal axis of insertion device 100 and/or guide member 110. In one example, laterally adjacent anchor channels 118 may be configured to direct vertebral anchors 300 along different exit trajectories. In the exemplary embodiment shown in FIGS. 11-14, anchor housing 116 may include three anchor channels 118. Two outer anchor channels 118 may be laterally offset from an inner anchor channel 118. The outer anchor channels 118 may urge respective vertebral anchors 300 along first exit trajectory 120 while the inner anchor channel 118 may urge a vertebral anchor 300 along second exit trajectory 122. Anchor channel 118 may further include a stop wall 146 (shown in FIGS. 18-23) that may extend radially inward from a wall of anchor channel 118. Stop wall 146 may be configured to abut a vertical wall of elongate portion 114 (of guide member 110) to prevent elongate portion 114 from being inserted too far distally into a patient by an operator. Thus, stop wall 146 also may prevent an inadvertent excessive force from being applied to intervertebral spacer 10 or to a vertebral body by elongate portion 114.

Anchor housing 116 may include one or more features to engage with corresponding features disposed on plate portion 14 of intervertebral spacer 10. In one example, an extension 117 (e.g., a cantilevered snap-fit extension 117) may extend longitudinally outward from the leading end (e.g., a distal face) of anchor housing 116. Extension 117 may include one or more surfaces configured to engage channel 50 of plate portion 14 in a snap fit or other suitable engagement. Anchor housing 116 also may include a threaded shank 113 that extends longitudinally outward from the leading endface of anchor housing 116. In some examples, threaded shank 113 may be received by bore 52 of plate portion 14. While snap-fit and threaded connections are disclosed in the examples shown by the figures, it should be noted that any other additional or alternative type of engagement may be utilized to couple anchor housing 116 to plate portion 14.

Anchor housing 116 also may include one or more positioning members 138, as shown in FIG. 18. Each positioning member 138 may secure a vertebral anchor 300 within a respective anchor channel 118. Thus, each anchor channel 138 may be associated with its own respective positioning member 118. In one example, positioning member 138 may be an elongate cantilever that is coupled to a leading end portion of anchor housing 116 via a linkage or hinge 140. In some examples, linkage or hinge 140 may be a spring-biased linkage or may be another suitable hinge or linkage. Positioning member 138 may extend from linkage 140 toward trailing end 102. At its proximal or trailing end, positioning member 138 may include a ramp 142 and an extension 144 spaced from ramp 142 by a recess. Ramp 142 may be an inclined surface configured to engage elongate portion 114 of guide member 110. Positioning member 138 may be configured to pivot about the linkage 140 and away from an interior of anchor channel 118 when ramp 142 is engaged by elongate portion 114 of guide member 110. In some examples, positioning member 138 may pivot in a direction that is opposite to the exit trajectory of its associated anchor channel 118. That is, if a given anchor channel 118 is configured to guide a vertebral anchor into a vertebral body along first trajectory 120, the associated positioning member 138 of that elongate channel may pivot about linkage 140 in the vertical direction that is opposite to the vertical vector of first trajectory 120. On the other hand, if a given anchor channel 118 is configured to guide a vertebral anchor 300 along the second trajectory 122, the associated positioning member 138 of that anchor channel 118 may be configured to pivot in a vertical direction that is opposite to the vertical vector of second trajectory 122. Extension 144 may include any suitable configuration (e.g., a ball or the like), and may be configured to be releasably coupled to a vertebral anchor 300 via groove 318.

Vertebral anchors 300 may be loaded into anchor channels 118 prior to the coupling of anchor housing 116 to plate portion 14 of intervertebral spacer 10. Vertebral anchors 300 may be loaded from either the trailing end or the leading end of anchor housing 116, if desired. In some examples, vertebral anchors 300 may be loaded by a spring-loaded block device. In one example, a vertebral anchor 300 may be loaded into the leading end of anchor housing 116 with trailing end 302 of the vertebral anchor being inserted first. That is, trailing end 302 of vertebral anchor 300 may be loaded into anchor channels 118 before leading end 304. Thus, vertebral anchors 300 may be loaded in a reverse manner such that the vertebral anchors 300 are loaded in the opposite direction to which they are inserted into the body. As vertebral anchors 300 are moved proximally through anchor channels 116, groove 318 may be coupled to extension 144 of positioning member 138. The docking, mating, or connection of extension 144 with groove 318 may fix vertebral anchor 300 within anchor channel 118 until vertebral anchor 300 is inserted through a vertebral body. In one example, extension 144 may be a ball and a groove 318 of vertebral anchor 300 may be a socket such that extension 144 and groove 318 form a ball and socket joint. However, those of ordinary skill in the art will appreciate that any other suitable form of releasable connection may be utilized.

Anchor housing 116 may be coupled to intervertebral spacer 10 to install vertebral anchors 300 into the body. Anchor housing 116 and plate portion 14 may be aligned via extension 117 and channel 50, and/or via shank 113 and bore 52 in such a manner as to align channels 118 of anchor housing 116 with bores 26 of plate portion 14. The alignment of channels 118 and bores 26 may permit one or more vertebral anchors 300 to be guided from a channel 118 through a corresponding bore 26 of plate portion 14, and into a vertebral body. Further, the anchor housing 116 and plate portion 14 may be aligned such that the exit trajectory of a given channel 118 may be aligned (e.g., collinear or coplanar) with the exit trajectory of an aligned bore 26. In some examples, the number of channels 118 disposed in anchor housing 116 may correspond exactly with the number of bores 26. However, it is contemplated that an exact correspondence may not exist between channels 118 and bores 26. For example, an anchor housing 116 may include fewer channels 118 than bores 26 in a plate portion. In such examples, anchor housing 116 may be coupled to plate portion 14 in a number of different configurations. In such examples, after a vertebral anchor 300 is inserted through a vertebral body, anchor housing 116 may be uncoupled from plate portion 14, reloaded with a new vertebral anchor 300, and recoupled to plate portion 14 at a different location.

With continuing reference to FIGS. 18-23, there is depicted an exemplary method of positioning a vertebral anchor 300 via insertion device 100. Referring to FIG. 18, vertebral anchor 300 is shown loaded into an anchor channel 118. The vertebral anchor 300 may be secured within the anchor channel 118 via the coupling of extension 144 with groove 318 of the vertebral anchor 300 as set forth above. Elongate portion 114 of guide member 110 then may be advanced distally (e.g., in the direction of leading end 304) such that the distal end of elongate portion 114 may contact ramp 142 (FIGS. 19 and 20). In some examples, stepped portion 132 of elongate portion 114 may contact the ramp 142. Elongate portion 114 may be advanced further distally, causing ramp 142 to slide vertically upward, thereby disengaging extension 144 from groove 318 of vertebral anchor 300 (FIG. 20). As elongate portion 114 is advanced further distally, the distal end of elongate portion 114 may abut the trailing end 302 of vertebral anchor (FIG. 21). In some examples, the stepped portion 132 of elongate portion 114 may abut head portion 306 of vertebral anchor 300. Uncoupled from extension 144, vertebral anchor 300 then may be advanced out of the leading end of anchor housing 116 and anchor channel 118 (FIG. 22) and ultimately inserted into a vertebral body (not shown) along a given exit trajectory (e.g., trajectory 120 or 122.), as shown in FIG. 23. After impacting one vertebral anchor 300 through a vertebral body, the same guide member 110 (and elongate portion 114) may be withdrawn and reinserted through a different elongate channel 108 and anchor channel 118 (having another preloaded vertebral anchor 300), to impact a different vertebral anchor 300, if desired. Alternatively, each set of elongate channels may include a dedicated guide member 110.

One embodiment of an insertion device 200 is shown in FIGS. 24-28. Insertion device 200 may extend from a first, trailing end 202 toward a second, leading end 204. A base portion 206 may include a proximal annular rim 208 and base shaft 209 extending therefrom. An alignment shaft 210 may extend from base shaft 209. In the example shown in FIG. 24 the leading end 204 of alignment shaft 210 may have a smaller diameter than the trailing end of alignment shaft 210, although other suitable configurations, including a substantially constant diameter shaft 210, are also contemplated. In some examples, alignment shaft 210 may include one or more longitudinally extending windows 218. In some examples, alignment shaft 210 may be a hollow elongate shaft accommodating a drive mechanism 216 therein. Drive mechanism 216 may be configured to actuate a coupling 222 disposed at the leading end of alignment shaft 210. Drive mechanism 216 may be a spring loaded drive shaft configured to reciprocally move coupling 222 between a retracted configuration and an extended configuration. While in the extended configuration, coupling 222 may engage with, e.g., bore 95 of intervertebral spacer 90 to couple insertion device 200 to intervertebral spacer 90. While coupling 222 is engaged to bore 95, drive mechanism 216 may move coupling 222 to the retracted configuration to disengage insertion device 200 from intervertebral spacer 90.

Coupling 222 may be disposed in an anchor housing 220 that is disposed at the leading end 204 of alignment shaft 210. Anchor housing 220 may include at least one anchor channel 224. Anchor channel 224 may include one or more features described with reference to anchor channel 118 of insertion device 100. For example, anchor channel 224 may have a variable cross-section along its length and may have a concave surface 230 (shown in FIGS. 26-28) that is complimentary to, e.g., elongate shank 408 of spacer 400 shown in FIG. 37. For example, a laterally extending portion of anchor channel 224 may receive a curved elongate shank 408. A guide member 228 that may be substantially similar to guide member 110 may be inserted through anchor channel 224 to assist with deploying an anchor disposed therein.

It is contemplated that insertion device 200 may include additional or alternative features for attaching to intervertebral spacer 90 such as, e.g., positive attachments, cam attachments, threaded attachments or other suitable attachments. In some examples, pins or other members also may prevent the rotation of insertion device 200 relative to intervertebral spacer 90 when the insertion device 200 and intervertebral spacer 90 are engaged. In some examples, the leading end of insertion device 200 may couple to the anterior face, lateral sides, or other regions of intervertebral spacer 90. In one embodiment, the insertion device 200 may include a stop that extends in either the cephalad or caudal direction of a centerline of insertion device 200 to prevent the intervertebral spacer 90 from being inadvertently impacted undesirably. That is, a stop may extend from the superior or inferior surface of insertion device 200 and may contact, e.g., a surface of the intervertebral spacer or vertebral body.

Anchor housing 220 may be coupled to an intervertebral spacer, e.g., intervertebral spacer 90, to install vertebral anchors 400 into the body. Anchor housing 220 and plate portion 92 may be aligned via coupling 222 and bore 95, in such a manner as to align channel 224 of anchor housing 220 with a bore 93 of plate portion 14. In some examples, anchor channels 224 may be laterally offset from the length of alignment shaft 210. The alignment of channel 224 and bore 93 may permit one or more vertebral anchors 400 to be guided from a channel 224 through a corresponding bore 93 of plate portion 92, and into a vertebral body. Further, the anchor housing 220 and plate portion 92 may be aligned such that the exit trajectory of a given channel 224 may be inline (e.g., collinear or coplanar) with the exit trajectory of an aligned bore 93. While only one anchor channel 224 is shown in the example of FIGS. 24-28, it is contemplated that additional anchor channels 224 may be utilized (e.g., a double or multi-barreled configuration) such that the number of channels 224 disposed in anchor housing 220 may correspond exactly with the number of bores 93 in vertebral spacer 90. In some examples, a guide member may extend through one or more anchor channels 224 to simultaneously insert one or more fastening members (e.g., vertebral anchors or screws) through one or more vertebral bodies. Other mechanisms of anchor insertion are also contemplated such as, e.g., a blocking set screw or leaf spring cutout of the spacer or plate that is flexible in the insertion direction and stiff in the expulsion direction. An associated intervertebral spacer also may include rotational stabilizers to add stability to the construct in vivo, and may contain radiographic markers to aid in interoperative visibility.

Figure 26:
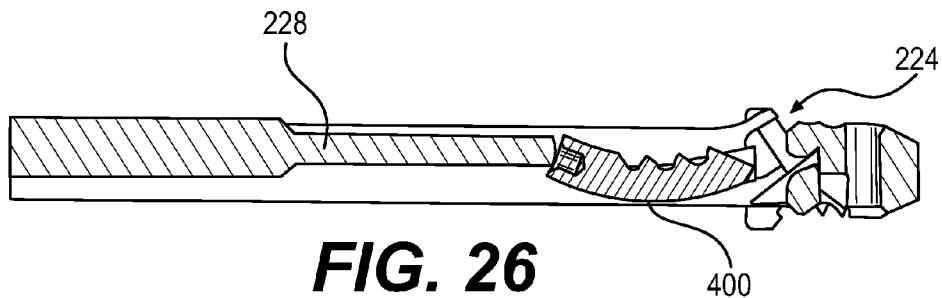
FIGS. 26-28 depict another exemplary method of installing a vertebral anchor in accordance with an example of the present disclosure.
Figure 27:
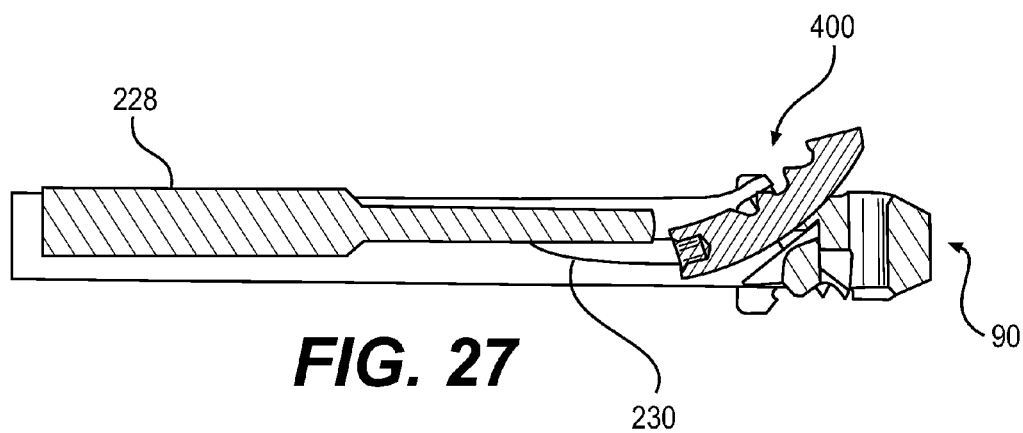
Figure 28:
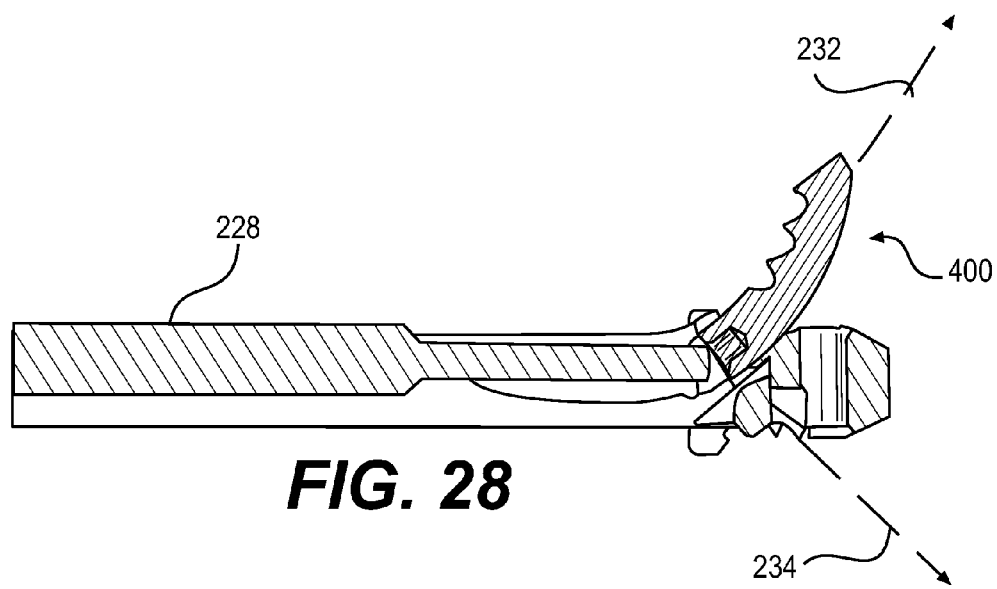
Figure 33:
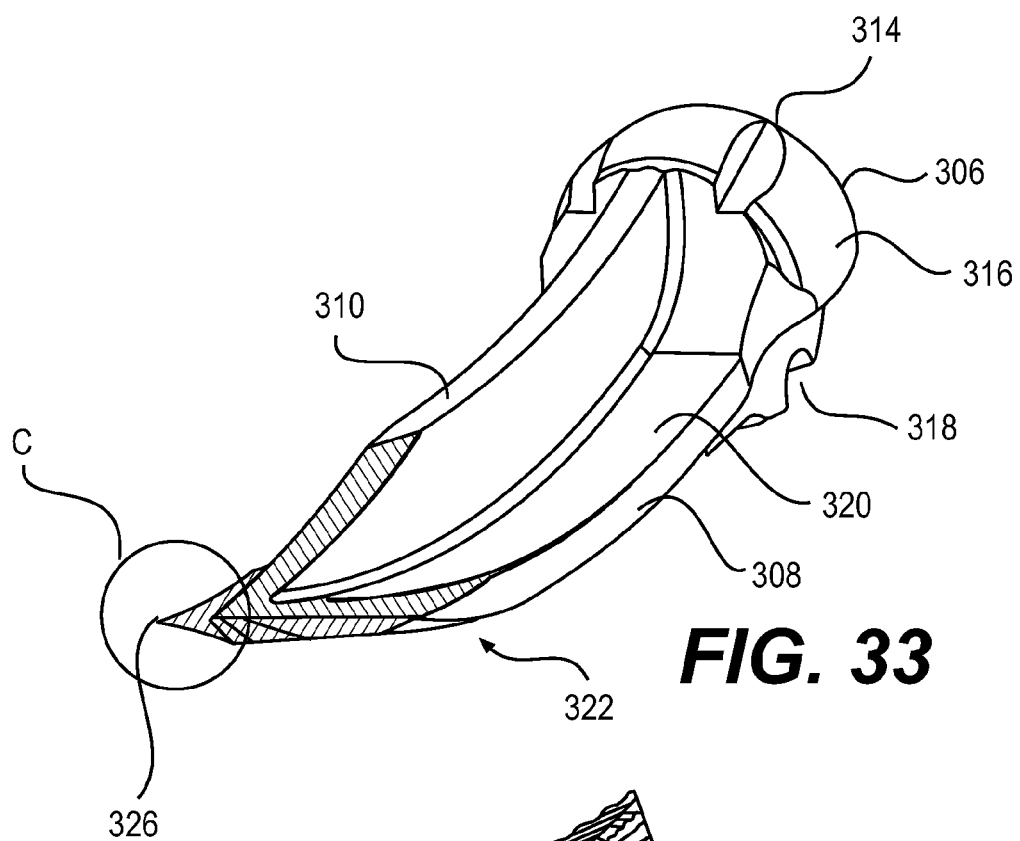
FIG. 33 is a perspective view of the vertebral anchor of FIG. 29.
Figure 34:
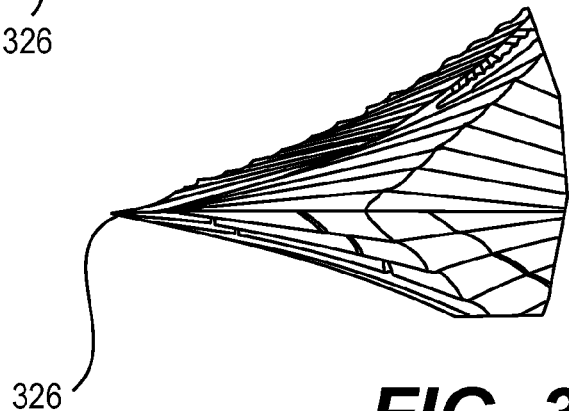
FIG. 34 is an enlarged view of detail C in FIG. 33, illustrating a distal portion of the vertebral anchor of FIG. 33.
Figure 35:
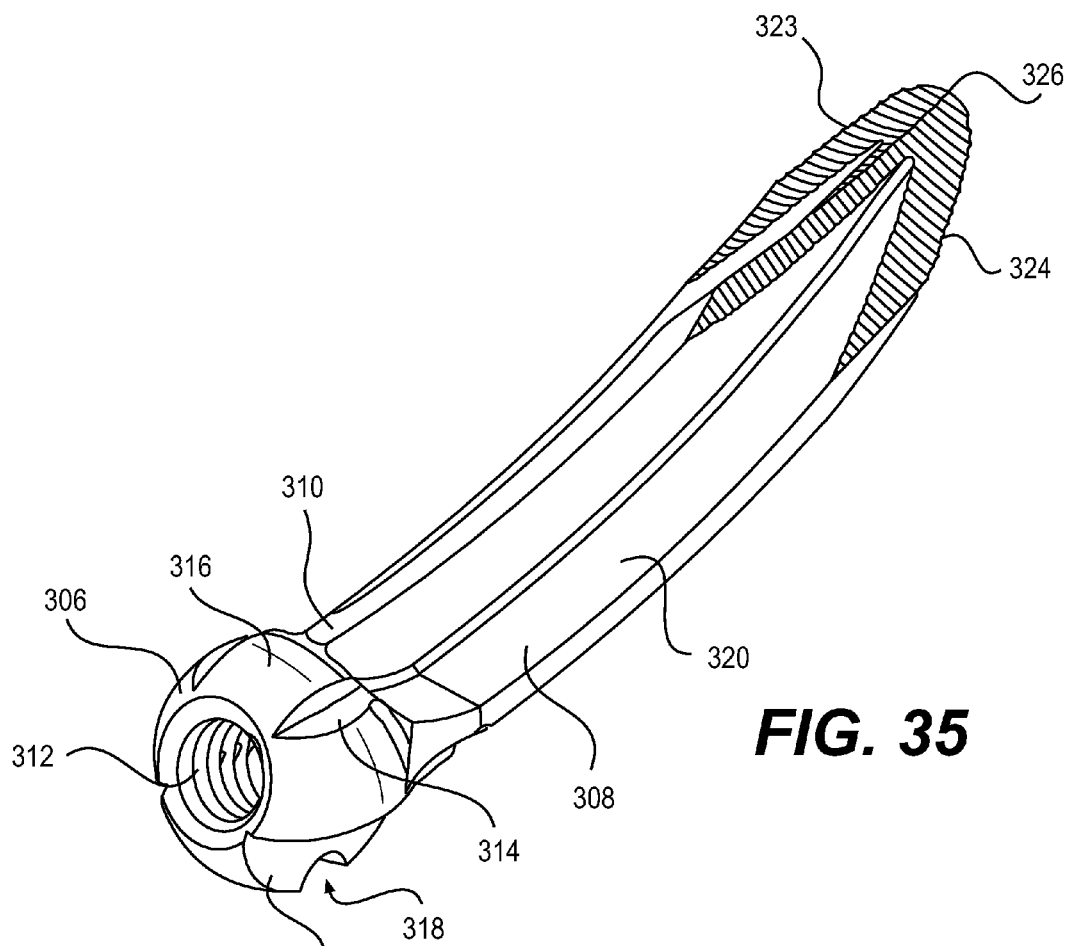
FIG. 35 is another perspective view of the vertebral anchor of FIG. 29.
Figure 36:
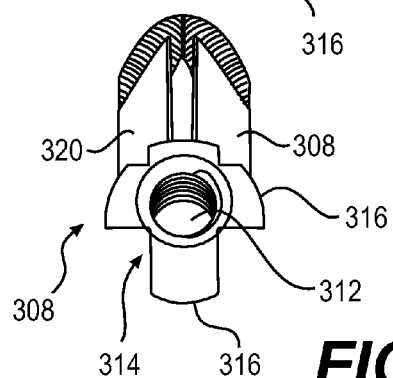
FIG. 36 is an end view of the vertebral anchor of FIG. 29.
Figure 37:
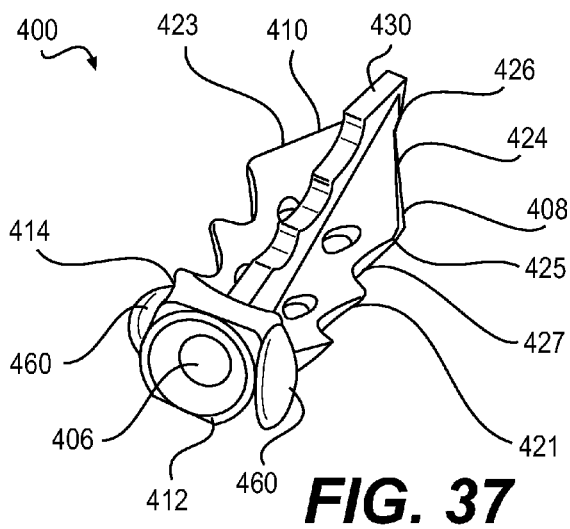
FIGS. 37-40 illustrate various views of another exemplary vertebral anchor in accordance with an example of the present disclosure.
Figure 40:
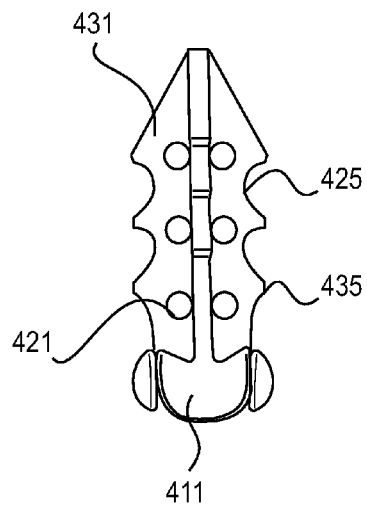
Figure 38:
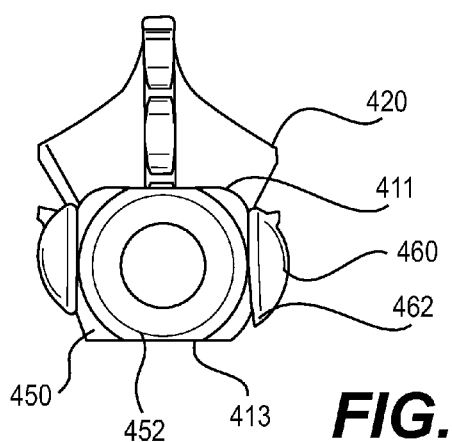
Figure 39:
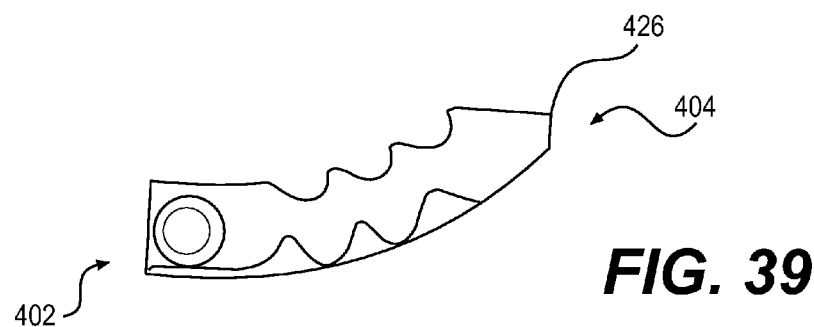

FIGS. 26-28 depict an exemplary method of positioning a vertebral anchor 400 via insertion device 200. Referring to FIG. 26, vertebral anchor 400 is shown loaded into an anchor channel 224. The vertebral anchor 400 may be secured within the anchor channel 224 by any suitable mechanism. Guide member 228 then may be advanced distally such that the distal end of guide member 228 may contact head portion 406 of vertebral anchor 400 (FIG. 26). Guide member 228 may extend from trailing end 202, through a trailing opening 226 (shown in FIG. 25) of anchor channel 224 to abut a vertebral anchor 400. Vertebral anchor 400 then may be advanced out of the leading end of anchor housing 220 and anchor channel 224 (FIG. 27) and ultimately inserted into a vertebral body (not shown) along a given exit trajectory, as shown in FIG. 28. After impacting one vertebral anchor 400 through a vertebral body, anchor housing 220 may be disengaged from plate portion 92, and another vertebral anchor 400 may be loaded into anchor channel 224. When anchor channel 224 is reloaded, anchor housing 220 may be re-engaged with plate portion 92 in a substantially similar manner as before, except that anchor channel 224 may be aligned with a different bore 93 of vertebral spacer 90.

A vertebral anchor 300 shown in FIG. 29 may extend from a first, trailing end 302 toward a second, leading end 304, and may include a head portion 306, an elongate shank 308, and an elongate fin 310. Vertebral anchor 300 may be formed from a rigid, bio-compatible material such as, e.g., titanium or polyetheretherketone (PEEK), among others. The head portion 306, elongate shank 308, and elongate fin 310 may be formed of the same or of different materials. Portions of vertebral anchor 300 may be treated with a titanium and/or hydroxyapatite plasma spray coating to encourage bony on-growth, improving the strength and stability of the connection between the respective component and the underlying bone (e.g., a vertebral body). Any other suitable coating also may be provided on one or more surfaces of vertebral anchor 300. Such coatings may include therapeutic agents (e.g., antibiotic coatings), if desired. Vertebral anchor 300 also may include radiopaque markings to facilitate in vivo visualization and insertion. Vertebral anchor 300 may be configured to be impacted into vertebral bodies to secure implants within the intervertebral space of a patient. Vertebral anchor 300 may be inserted into the patient and impacted through the bone of a vertebral body.

The head portion 306 may be disposed at trailing end 302 of vertebral anchor 300 and may be generally spherical or ball shaped. In some examples, the head portion 306 may be shaped in a substantially similar manner as the head portion of other vertebral fastening members (e.g., bone screws). In some examples, the head portion 306 may include a bore 312 to facilitate removal of vertebral anchor 300 from a vertebral body. In some examples, bore 312 may be a threaded bore or may include other suitable features to facilitate the extraction of vertebral anchor 300 from a vertebral body by, e.g., a pulling tool or the like. In some examples, a tool with a threaded tip may be rotated to threadingly engage bore 312, and the tool may be linearly withdrawn to extract vertebral anchor 300 from within a vertebral body. The pooling tool also may include one or more of a cam attachment, an expandable driver, or another feature for removing vertebral anchor 300. A plurality of slots or notches 314 may be formed in the outer periphery of head portion 306. In some examples, a plurality of flanges 316 may define the plurality of slots 314 about the outer periphery of the head portion 306. The flanges 316 may be disposed around head portion 306 to form a generally t-shaped cross-section. A groove 318 (e.g., a semi-cylindrical groove) may be formed in the outer periphery of head portion 306. In some examples, the groove 318 may be disposed within one of the flanges 316, or in another suitable location on head portion 306. In some examples, one or more grooves 318 may be disposed along the periphery of head portion 306. Groove 318 may cooperate with an extension (e.g., extension 144 shown in FIG. 18) of an installation device as discussed above. In some examples, the flanges 316 and slots 314 of the head portion 306 may cooperate with or be received by complimentary shaped features in a spacer, implant, plate system or the like. The interaction between the flanges 316, slots 314, and the complimentary-shaped features may prevent the relative rotation of vertebral anchor 300 before, during and/or after installation of vertebral anchor 300 into a vertebral body.

Elongate shank 308 may extend away from the head portion 306 toward the leading end 304. In some examples, elongate shank 308 may be planar and may exhibit a curvature as it extends away from the head portion 306. That is to say, in some examples, elongate shank 308 may include a curvilinear configuration. Specifically, elongate shank 308 may be curved (e.g., symmetrically curved) about a longitudinal axis. More specifically, elongate shank 308 exhibit a curvature about a median longitudinal axis. Further, the elongate shank 308 may be curved such that a concave surface 320 and a convex surface 322 extend from trailing end 302 toward leading end 304. The leading end of the elongate shank 308 may be formed by a pair of inclined surfaces 323 and 324 that extend from the lateral ends of elongate shank 308 toward an apex 326. Apex 326 may be disposed on a longitudinal axis of vertebral anchor 300. Thus, at leading end 304, elongate shank 308 may be formed as a projectile point, arrowhead, bladed edge, cutting edge, or the like to facilitate impaction and insertion through bone and/or tissue. To reduce impaction force, the apex 326 may feature a hollow style which may be similar to a knife edge. That is, the edge or apex 326 of the anchor may approach a shallow angle, e.g., approximately 15 degrees at the sharpest point, which may increase closer to a central axis. In some examples, apex 326 may be rounded to prevent injury, but may still be sharp around its edges. To further reduce insertion force and manufacturing time, the hollow surfaces may be surface machined using, e.g., a 1 mm full radius mill and, e.g., a 0.25 mm step-over, which may result in the wavy surface (including a plurality of rolling peaks and valleys) along the face of the hollow surface. As further shown in FIGS. 29-36, inclined surfaces 123 and 124 may include one or more geometric features, such as, e.g., serrations (shown in FIG. 30), teeth, tapers, bevels or the like to further facilitate spearing, cutting, slicing, or impacting of elongate shank 308 through bone and/or tissue. Inclined surfaces 323 and 324 also may be formed with an edge (e.g., a v-edge, beveled edge, chisel edge, convex edge or the like) to facilitate impaction.

Elongate fin 310 also may extend away from head portion 306 toward the leading end 304 of vertebral anchor 300. Elongate fin 310 also may extend away from the concave surface 320 of the elongate shank 308. The vertical periphery of elongate fin 310 may be defined by a concave surface 328. In some examples, the elongate shank 308 and elongate fin 310 may be generally orthogonal to one another and may form a generally t-shaped cross-section. The t-shaped cross-section formed by elongate shank 308 and elongate fin 310 may reduce impaction forces of vertebral anchor 300, and may increase the torsional stability of vertebral anchor 300 as compared to anchors having planar cross-sections. At leading end 304, elongate fin 310 may include a ramped surface 130 that extends toward apex 326. Ramped surface 330 may include one or more of the geometrical features described with reference to inclined surfaces 323 and 324. In some examples, a vertical periphery of ramp 130 may be beveled and/or have a v-shaped cross-section.

Turning now to FIGS. 37-40, a further embodiment of a vertebral anchor 400 is depicted. Vertebral anchor 400 may extend from a first, trailing end 402 toward a second, leading end 404, and may include a head portion 406, an elongate shank 408, and an elongate fin 428. Vertebral anchor 400 may be formed from one or more of the materials used to form vertebral anchor 300 and may be treated with one or more similar coatings, if desired. Vertebral anchor 400 may be inserted into a patient and impacted through bone of a vertebral body.

The head portion 406 may be disposed at trailing end 402 of vertebral anchor 400 and may have a partially spherical outer periphery. In some examples, the head portion 406 may be formed by a plurality of spherical segments formed by removing one or more spherical caps from the spherical outer periphery of head portion 406. In the embodiments shown in FIGS. 37-40, at least three planar surfaces 411, 413, and 450 may define at least a portion of the outer periphery of the partially-spherical head portion 406. In one example, planar surfaces 411 and 413 may be substantially parallel to one another, and may be substantially orthogonal to planar surface 450. In some examples, planar surface 450 may define the proximal-most portion of head portion 406 and of vertebral anchor 400. That is, planar surface 450 may define the surface that is furthest toward trailing end 402 of vertebral anchor 400. A recess (e.g., a concave recess) 452 may be disposed within planar surface 450 such that planar surface 450 may be defined by interrupted hemispherical arc portions, as seen in FIG. 32. A bore 412 may have an opening disposed within recess 452. Bore 412 may extend through head portion 406 and may include one or more features described with reference to bore 312 of vertebral anchor 300. While not shown in FIGS. 37-40, it is contemplated that head portion 406 may include other features described with reference to head portion 306 of vertebral anchor 300, such as, e.g., grooves and/or mating features configured to secure and position vertebral anchor 400 within an anchor channel of an insertion device.

Head portion 406 also may include one or more protrusions 460 that may extend away from the outer periphery of head portion 406. In the examples shown, protrusions 460 may be formed as spherical caps (e.g., partial domes), although protrusions 460 may be formed in any other suitable configuration. In some examples, the base of protrusions 460 may include an annular rim 462 that may, e.g., extend radially away from protrusions 460. In some examples, head portion 406 may include two protrusions 460 that extend in opposite directions. It is contemplated that another suitable number of protrusions 460 may be employed in alternative configurations.

Elongate shank 408 may extend away from the head portion 406 toward the leading end 404. In some examples, elongate shank 408 may be planar and may exhibit a curvature as it extends away from the head portion 406. In some examples, elongate shank 408 may be curved (e.g., symmetrically curved) about a longitudinal axis. More specifically, elongate shank 408 may exhibit a curvature about a median longitudinal axis. Further, the elongate shank 408 may be curved such that a concave surface 420 and a convex surface 422 extend from trailing end 402 toward leading end 404. The leading end of the elongate shank 408 may be formed by a pair of inclined surfaces 423 and 424 that extend from the lateral ends of elongate shank 408 toward an apex 426. Apex 426 may be disposed on a longitudinal axis of vertebral anchor 400. In some embodiments, apex 426 may include a curvilinear periphery. Thus, at leading end 404, elongate shank 408 may be formed to include any of the suitable geometries and features disposed on vertebral anchor 300 to facilitate impaction.

In one example, the lateral sides of elongate shank 408 may include one or more cutouts 421. For example, each lateral side of elongate shank 408 may include two cutouts 421 to form one or more keels 425. The keels 425 may generally extend and point in a reverse manner with respect to a remainder of vertebral anchor 400. That is, the end points of the keels 425 may be oriented toward the trailing end 402 and not leading end 404. Thus, keels 425 may assist in inhibiting vertebral anchor 400 from exiting a vertebral body once inserted therein. In the embodiment shown in FIGS. 31-34, each lateral side of elongate shank 408 may include two cutouts 421 and three keels 425, although any other suitable combination of cutouts and keels may be utilized.

One or more apertures 427 may disposed through the surface of elongate shank 408. Though depicted as through-holes, apertures 427 also may include blind recesses disposed in one or more surfaces of elongate shank 308. Once inserted through the bone of a vertebral body, apertures 427 may encourage bony in-growth or on-growth therein, further securing vertebral anchor 400 within a respective vertebral body. In some examples, apertures 427 may be packed with bone graft or other bone-growth inducing substances.

Elongate fin 428 also may extend away from head portion 406 toward the leading end 404 of vertebral anchor 400. Elongate fin 428 also may extend away from the concave surface 3120 of the elongate shank 408. The vertical periphery of elongate fin 428 may be defined by one or more cutouts 431 and keels 435 in a substantially similar manner as the lateral sides of elongate shank 408. In some examples, the elongate shank 408 and elongate fin 428 may be generally orthogonal to one another and may form a generally t-shaped cross-section. The t-shaped cross-section formed by elongate shank 408 and elongate fin 428 may reduce impaction forces of vertebral anchor 400, and may increase the torsional stability of vertebral anchor 400 as compared to anchors having planar cross-sections. At leading end 404, elongate fin 428 may include a ramped surface 430 that extends toward apex 426. Ramped surface 430 may include one or more of the geometrical features described with reference to inclined surfaces 423 and 424. In some examples, apertures (not shown but similar to apertures 427) may be disposed on or through elongate fin 428 to encourage bony in-growth or on-growth therein.

In some examples, vertebral anchors 300 and 400 may facilitate easy insertion of various vertebral spacers (e.g., stand-alone ACDF and/or ALIF spacers) through the use of inline impaction of anchors 300 and 400 through the spacer. In some examples, the inline operation may be facilitated through appropriate implant design, instrument design, and design of the implant-instrument interface. In some examples, the various examples of the present disclosure may permit the use of stand-alone spacers at the most caudal or most cephalad cervical disc spaces (e.g., C5-C6/C6-C7 and C2-C3), and at the caudal lumbar levels (e.g., L5-S1) where angled instruments may pose insertion problems due to interference with tissue or other anatomy.

Any aspect set forth in any example may be used with any other example set forth herein. Every device and apparatus set forth herein may be used in a suitable medical procedure, such as, e.g., a vertebral disc replacement procedure, and may be advanced through any suitable body lumen, body cavity, or incision.

It will be apparent to those skilled in the art that various modifications and variations can be made in the disclosed systems and processes without departing from the scope of the disclosure. Other examples of the disclosure will be apparent to those skilled in the art from consideration of the specification and practice of the disclosure disclosed herein. It is intended that the specification and examples be considered as exemplary only.

We claim:

1. A vertebral anchor, comprising:
    a head portion;
    an elongate shank extending from the head portion; and
    an elongate fin extending from the head portion and along a surface of the elongate shank, the elongate shank and the elongate fin forming a generally t-shaped cross-section,
    wherein an outer periphery of the head portion is at least partially spherical such that curved outer surfaces extend around a circumference of the head portion and an upper end of the head portion is generally planar,
    wherein the elongate shank further includes a concave surface.

2. The vertebral anchor of claim 1, wherein the elongate fin extends along the concave surface of the elongate shank.

3. The vertebral anchor of claim 1, wherein a leading end of the elongate shank is formed by two inclined edges that converge laterally inward toward a leading apex.

4. The vertebral anchor of claim 3, wherein the elongate fin includes a ramp that converges toward the leading apex.

5. The vertebral anchor of claim 3, wherein the ramp is serrated.

6. The vertebral anchor of claim 3, wherein the two inclined edges are serrated.

7. The vertebral anchor of claim 1, wherein the head portion includes a bore.

8. The vertebral anchor of claim 1, wherein the head portion includes a groove disposed in an outer periphery.

9. The vertebral anchor of claim 1, wherein an outer periphery of the head portion includes one or more notches.

10. The vertebral anchor of claim 9, wherein the head portion includes a pair of protrusions that extend away from the head portion in opposite directions.

11. The vertebral anchor of claim 9, wherein the elongate shank includes one or more apertures configured to promote bony-ingrowth when the vertebral anchor in inserted through a vertebral body.

12. The vertebral anchor of claim 9, wherein lateral sides of the elongate shank include one or more cutouts.

13. The vertebral anchor of claim 12, wherein the cutouts of the elongate shank form one or more keels.

14. A vertebral anchor, comprising:
    a partially-spherical head portion having curved outer surfaces that extend around a circumference of the head portion and an upper end that is generally planar and a locking groove disposed in an outer periphery of the head portion, the locking groove being configured to form a ball and socket joint with a ball of a positioning member;
    an elongate shank extending from the head portion, the elongate shank having a first concave surface and a pair of inclined edges formed in a blade-like configuration; and
    an elongate fin extending from the head portion and along the first concave surface of the elongate shank, a vertical periphery of the elongate fin having a second concave surface, and a ramp disposed at a leading end of the elongate fin that intersects the pair of inclined surfaces of the elongate shank.

15. The vertebral anchor of claim 14, wherein the inclined edges of the elongate shank and the ramp of the elongate fin intersect at a distal most point of the vertebral anchor.

16. The vertebral anchor of claim 14, wherein a portion of each of the inclined edges and the ramp are serrated.

17. A vertebral anchor, comprising:
a trailing end and a leading end;
a partially-spherical head portion at the trailing end having curved outer surfaces that extend around a circumference of the head portion and an upper end that is generally planar and one or more protrusions extending from an outer periphery;
an elongate shank extending from the head portion toward the leading end, the elongate shank having a concave surface, wherein the lateral sides of the elongate shank include one or more inward-extending cutouts; and
an elongate fin extending from the head portion and along the concave surface of the elongate shank, a vertical periphery of the elongate fin having a concave surface, and wherein a vertical periphery of the elongate fin includes one or more inward-extending cutouts.

18. The vertebral anchor of claim 17, wherein the cutouts of the elongate shank form one or more keels extending toward the trailing end of the vertebral anchor.

\* \* \* \* \*